(12) United States Patent
Whitsett et al.

(10) Patent No.: US 10,159,716 B2
(45) Date of Patent: *Dec. 25, 2018

(54) SURFACTANT PROTEIN D FOR THE TREATMENT OF DISORDERS ASSOCIATED WITH LUNG INJURY

(71) Applicant: Children's Hospital Medical Center, Cincinnati, OH (US)

(72) Inventors: Jeffrey A. Whitsett, Cincinnati, OH (US); Machiko Ikegami, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/341,383

(22) Filed: Nov. 2, 2016

(65) Prior Publication Data

US 2017/0136099 A1    May 18, 2017

Related U.S. Application Data

(63) Continuation of application No. 14/062,682, filed on Oct. 24, 2013, now Pat. No. 9,492,503, which is a continuation of application No. 13/366,144, filed on Feb. 3, 2012, now abandoned.

(60) Provisional application No. 61/439,760, filed on Feb. 4, 2011.

(51) Int. Cl.
| | | |
|---|---|---|
| *A61K 38/00* | (2006.01) | |
| *C07K 14/785* | (2006.01) | |
| *A61K 38/17* | (2006.01) | |

(52) U.S. Cl.
CPC ........ *A61K 38/395* (2013.01); *A61K 38/1732* (2013.01)

(58) Field of Classification Search
None
See application file for complete search history.

(56) References Cited

U.S. PATENT DOCUMENTS

| | | | |
|---|---|---|---|
| 5,670,328 A | 9/1997 | Inoue et al. | |
| 6,013,619 A | 1/2000 | Cochrane et al. | |
| 6,046,158 A | 4/2000 | Ariizumi et al. | |
| 6,180,142 B1 | 1/2001 | Taeusch | |
| 6,838,428 B2 | 1/2005 | Whitsett | |
| 8,865,643 B2 | 10/2014 | Clark | |
| 8,883,730 B2 | 11/2014 | Mahajan | |
| 8,933,032 B2 * | 1/2015 | Whitsett | A61K 38/17 424/557 |
| 9,370,555 B2 | 6/2016 | Whitsett et al. | |
| 9,492,503 B2 * | 11/2016 | Whitsett | A61K 38/395 |
| 2004/0037781 A1 | 2/2004 | McCormack, Jr. | |
| 2008/0242615 A1 * | 10/2008 | Ikegami | A61K 38/395 514/1.5 |
| 2015/0182599 A1 | 7/2015 | Whitsett | |

FOREIGN PATENT DOCUMENTS

| | | |
|---|---|---|
| WO | WO 91/00871 | 1/1991 |
| WO | WO 94/23582 | 10/1994 |
| WO | WO 98/46245 | 10/1998 |
| WO | WO 03/035679 | 5/2003 |
| WO | WO 05/072340 | 8/2005 |
| WO | WO 06/128025 | 11/2006 |

OTHER PUBLICATIONS

Sato et al. "Surfactant Protein-D Inhibits Lung Inflammation Caused by Ventilation in Premature Newborn Lambs" Am. J. Resp. Crit. Care Med. 181:1089-1105. (Year: 2010).*
Ikegami et al. "Surfactant Protein-D and Surfactant Inhibit Endotoxin-Induced Pulmonary Inflammation" Chest 132:1447-1454. (Year : 2007).*
Aderibigbe, et al., 1999. Brief exposure to 95% oxygen alters surfactant protein D and mRNA in adult rat alveolar and bronchiolar epithelium. *Am J Respir Cell Mol Biol.* 20(2):219-227.
Awasthi, et al. 1999 Surfactant proteins A and D in premature baboons with chronic lung injury (Bronchopulmonary dysplasia). Evidence for an inhibition of secretion. *Am J Respir Crit Care Med.* 160(3):942-949.
Bachurski, et al. 2003. Nuclear factor I/thyroid transcription factor 1 interactions modulate surfactant protein C transcription. *Mol. Cell. Biol.* 23:9014-9024.
Belperio JA, et al. Critical role for CXCR2 and CXCR2 ligands during the pathogenesis of ventilator-induced lung injury. *J Clin Invest* 2002; 110:1703-1716.
Besnard et al., 2005. Stage-specific regulation of respiratory epithelial cell differentiation by Foxa1. *Am. J. Physiol.* 289:L750-L759.
Bland et al., 1989. Lung fluid balance in lambs before and after premature birth. *J Clin Invest*, 84(2):568-576.
Bohinski, et al., 1994. The lung-specific surfactant protein B gene promoter is a target for thyroid transcription factor 1 and hepatocyte nuclear factor 3, indicating common factors for organ-specific gene expression along the foregut axis. *Mol. Cell. Biol.* 14:5671-5681.
Borron et al. 1998. Recombinant rat surfactant-associated protein D inhibits human T lymphocyte proliferation and IL-2 production. *The Journal of Immunology*, 161:4599-4603.
Botas, et al. 1998. Altered surfactant homeostasis and alveolar type II cell morphology in mice lacking surfactant protein D. *Proc. Natl. Acad. Sci. USA*, 95(20):11869-11874.
Bruno, et al., 1995. Lung cell-specific expression of the murine surfactant protein A (SP-A) gene is mediated by interactions between the SP-A promoter and thyroid transcription factor-1. J. Biol. Chem. 270:6531-6536. Erratum in: J. Biol. Chem. 1995 270(12): 16482.

(Continued)

*Primary Examiner* — Zachary J Miknis
(74) *Attorney, Agent, or Firm* — Knobbe, Martens, Olson & Bear LLP

(57) ABSTRACT

Surfactant protein D (SP-D) is a member of the collectin family of collagenous lectin domain-containing proteins that is expressed in epithelial cells of the lung. Described herein are methods and compositions for the treatment of disorders associated with lung injury, including methods and compositions for the treatment of bronchopulmonary disorder (BPD).

20 Claims, 6 Drawing Sheets

Specification includes a Sequence Listing.

(56) References Cited

OTHER PUBLICATIONS

Cao, et al., 2004. IL-4 induces production of the lung collectin surfactant protein-D. *J Allergy Clin Immunol.* 113(3):439-444.
Clark, et al. 2002 Surfactant protein D reduces alveolar macrophage apoptosis in vivo. *J Immunol.* 169(6):2892-2899.
Clark, et al. 2002. Structural requirements for SP-D function in vitro and in vivo: therapeutic potential of recombinant SP-D. *Immunobiology.* 205(4-5):619-631.
Clark, et al., 2003. The potential of recombinant surfactant protein-D therapy to reduce inflammation in neonatal chronic lung disease, cystic fibrosis, and emphysema. *Arch Dis Child.* 88(11):981-984.
Clark, et al., Targeted disruption of the surfactant protein B gene disrupts surfactant homeostasis causing respiratory failure in newborn mice, Proc Natl Acad Sci U S A 1995 92:7794-8.
Crouch, 1998. Collectins and pulmonary host defense, *Am J Resp Cell and Mol Bio*, 19:177-201.
Crouch, 2000 Surfactant protein-D and pulmonary host defense. *Respir. Res.*, 1:93-108.
Crouch, et al. 2001 Surfactant proteins A and D and pulmonary host defense. *Annu Rev Physiol.* 63:521-554.
Crouch, et al., 1991. Developmental expression of pulmonary surfactant protein D (SP-D). *Am J Respir Cell Mol Biol.* 5(1):13-18.
Crouch, et al., 1992. Surfactant protein D: subcellular localization in nonciliated bronchiolar epithelial cells. *Am J Physiol.* 263(1 Pt 1):L60-L66.
Crouch, et al., 1993. Genomic organization of human surfactant protein D (SP-D). *The Journal of Biological Chemistry*, 268(4):2976-2983.
Crouch; 1998.Structure, biologic properties, and expression of surfactant protein D (SP-D). *Biochim Biophys Acta.* 1408(2-3):278-289.
Davé, et al., 2004. Nuclear factor of activated T cells regulates transcription of the surfactant protein D gene (Sftpd) via direct interaction with thyroid transcription factor-1 in lung epithelial cells. *J Biol Chem.* 279(33):34578-34588.
De Felice, et all., 2003. TTF-1 phosphorylation is required for peripheral lung morphogenesis, perinatal survival, and tissue-specific gene expression. *J. Biol. Chem.* 278:35574-35583.
Dong et al., 1998. Degradation of surfactant protein D by alveolar macrophages. *Am J Physiol.* 274(1 Pt 1)L97-105.
Eggleton, et al. 1999. Lung surfactant proteins involved in innate immunity. *Current Opinion in Immunology*, 11(1):28-33.
Endo, et al., 2002. Surfactant protein A and D (SP-A, AP-D) levels in patients with septic ARDS. *Res Commun Mol Pathol Pharmacol.* 111(5-6):245-251.
Erpenbeck, et al., 2005. Surfactant protein D increases phagocytosis and aggregation of pollen-allergen starch granules. *Am J Physiol Lung Cell Mol Physiol.* 288(4):L692-698.
Fisher, et al., 1995. Expression of pulmonary surfactant protein D in rat gastric mucosa. *Am J Respir Cell Mol Biol.* 12(1):13-18.
Fisher, et al., 2000. Pulmonary-specific expression of SP-D corrects pulmonary lipid accumulation of SP-D gene-targeted mice. *Am. J. Physiol. Lung Cell. Mol. Physiol.*, 278(2):L365-L373.
Fujita, et al. 2005. Serum surfactant protein D is increased in acute and chronic inflammation in mice. *Cytokine* 31(1):25-33.
Gardai, et al., 2003. By binding SIRPalpha or calreticulin/CD91, lung collectins act as dual function surveillance molecules to suppress or enhance inflammation. *Cell.* 115(1):13-23.
Greene, et al., 1999. Serial changes in surfactant-associated proteins in lung and serum before and after onset of ARDS. *Am J Respir Crit Care Med.* 160(6):1843-1850.
Greene, et al., 2002. Serum surfactant proteins-A and -D as biomarkers in idiopathic pulmonary fibrosis. *Eur Respir J.* 19(3):439-446.
Haczku, et al., 2004. Surfactant protein D and asthma. *Clin Exp Allergy.* 34(12):1815-1818.

Hansen, et al., 2006. Surfactant protein D augments bacterial association but attenuates major histocompatibility complex class II presentation of bacterial antigens. *Am J Respir Cell Mol Biol.* 36(1):94-102.
Hartl, et al., 2006. Surfactant protein D in human lung diseases. *Eur J Clin Invest.* 36(6):423-435.
Hartshorn, et al. 1996. Interactions of recombinant human pulmonary surfactant protein D and SP-D multimers with influenza A. *Am J Physiol Lung Cell Mol Physiol.* 271:L753-L762.
Hartshorn, et al. 1998. Pulmonary surfactant proteins A and D enhance neutrophil uptake of bacteria. *Am J Physiol.* 274(6 Pt 1):L958-L969.
Hartshorn, et al. 2000. Enhanced anti-influenza activity of a surfactant protein D and serum conglutinin fusion protein. *American Journal of Physiology*, 278(1):L90-L98.
Hartshorn, et al., 1994. Evidence for a protective role of pulmonary surfactant protein S (SP-D) against influenza A virus. *J Clin Invest.*, 94(1):311-319.
Hawgood, et al. 2001. The pulmonary collectins and surfactant metabolism. *Annu Rev Physiol.* 63:495-519.
He, et al., 2000. Proximal promoter of the surfactant protein D gene: regulatory roles of AP-1, forkhead box, and GT box binding proteins. *J Biol Chem.* 275(40):31051-31060.
Herbein, et al., 2000. Binding and uptake of surfactant protein D by freshly isolated rat alveolar type II cells. *Am J Physiol Lung Cell Mol Physiol.* 278(4):L830-L839.
Hickling, et al. 1999. A recombinant trimeric surfactant protein D carbohydrate recognition domain inhibits respiratory syncytial virus infection in vitro and in vivo. *European Journal of Immunology*, 29(11):3478-3484.
Hokuto, et al., 2004. Stat-3 is required for pulmonary homeostasis during hyperoxia. *J Clin Invest.* 113(1):28-37.
Honda, et al. 1995. Pulmonary surfactant protein D in sera and bronchoalveolar lavage fluids. *Am J Respir Crit Care Med.* 152(6 Pt 1):1860-1866.
Ikegami M, et al. Characteristics of surfactant from SP-A deficient mice. *Am J Physiol Lung Cell Mol Physiol* 1998;275:L247-L25.
Ikegami M, et al. Intratracheal recombinant surfactant protein D prevents endotoxin shock in the newborn preterm lamb. *Am J Respir Crit Care Med* 2006; 173:1342-1347.
Ikegami M, et al. Surfactant protein-D and surfactant inhibit endotoxin induced pulmonary inflammation. *Chest* 2007; 132:1447-1454.
Ikegami M, et al. Surfactant protein-D regulates the postnatal maturation of pulmonary surfactant lipid pool sizes. *J Appl Physiol* 2009; 106:1545-1552.
Ikegami M, Jobe A. Postnatal lung inflammation increased by ventilation of preterm lambs exposed antenatally to *Escherichia coli* endotoxin. *Pediatr Res* 2002; 52:356-362.
Ikegami M, Jobe AH. Surfactant metabolism. *Semin Perinatol* 1993;17:233-240.
Ikegami, et al., 1980. The quantity of natural surfactant necessary to prevent the respiratory distress syndrome in premature lambs. *Pediatr Res.* 14(9):1082-1085.
Ikegami, et al., 1981. Phospholipid composition of fetal lung fluid and amniotic fluid during late gestation in sheep. *Am J Obstet Gynecol.* 141(2):227-229.
Ikegami, et al., 1993. Surfactant metabolism. *Semin Perinatol.* 17(4):233-240.
Ikegami, et al., 2000. Surfactant metabolism in SP-D gene-targeted mice. *Am J Physiol Lung Cell Mol Physiol.* 279(3):L468-L476.
Ikegami, et al., 2004. Initial responses to ventilation of premature lambs exposed to intra-amniotic endotoxin 4 days before delivery. *Am J Physiol Lung Cell Mol Physiol.* 286(3):L573-L579.
Jain-Vora, et al. 1998. Interleukin-4 enhances pulmonary clearance of pseudomonas aeruginosa, *Infection and Immunity*, 66(9):4229-4236.
Jain-Vora, et al., 1997. Interleukin-4 alters epithelial cell differentiation and surfactant homeostasis in the postnatal mouse lung. *Am. J. Respir. Cell. Mol. Biol.* 17:541-551.
Jobe et al., 1985. Lung protein leaks in ventilated lambs: effects of gestational age. *J Appl Physiol.* 58(4):1246-1251.
Jobe, A.H. 1993 Pulmonary Surfactant Therapy, N Engl J Med, 328:861-868.

(56) References Cited

OTHER PUBLICATIONS

Jobe, et al. 1997. Surfactant for the treatment of respiratory distress syndrome. *Am. Rev. Respir. Dis.* 136:1256-1275.
Jobe, et al., 1996. Surfactant effects on aerosolized and instilled adenoviral-mediated gene transfer. *Hum Gene Ther.* 7(6):697-704.
Johansson, et al. 1994. The protein of the surfactant system. *Eur. Respir. J.*, 7:372-391.
Kasper, et al., 2002. Increased surfactant protein D in rat airway goblet and Clara cells during ovalbumin-induced allergic airway inflammation. *Clin Exp Allergy*. 32(8):1251-1258.
Kelly, et al., 1996. Transcription of the lung-specific surfactant protein C gene is mediated by thyroid transcription factor 1. J. Biol. Chem. 271(12):6881-6888.
Kingma, et al., 2006. Correction of pulmonary abnormalities in Sftpd-/-mice requires the collagenous domain of surfactant protein D. *J Biol Chem*. 281(34):24496-24505.
Kishore, et al. 1996. The α-helical neck region of human lung surfactant protein D is essential for the binding of the carbohydrate recognition domains to lipopolysaccharides and phospholipids. *Biochem J.* 318(Pt 2):505-511.
Kitamura, et al., 2003. Study of surfactant protein D (SP-D) in spetic ards: report of three cases. *Critical care and shock, Indonesian Society of Critical Care Medicine.* 6(2):114-117.
Korfhagen, et al. 1996. Altered surfactant function and structure in SP-A gene targeted mice. *Proc. Natl. Acad. Sci. USA*, 93:9594-9599.
Korfhagen, et al. 1998. Surfactant protein-D regulates surfactant phospholipid homeostatis in vivo. *The Journal of Biological Chemistry*, 273(43):28438-28443.
Kramer BW, et al. Surfactant protein A recruits neutrophils into the lungs of ventilated preterm lambs. *Am J Respir Crit Care Med* 2001; 163:158-165.
Kramer, et al. 2001. Exogenous surfactant changes the phenotype of alveolar macrophages in mice. *Am J Physiol Lung Cell Mol Physiol.* 280(4):L689-L694.
Kramer, et al., 2001. Surfactant protein A recruits neutrophils into the lungs of ventilated preterm lambs. *Am J Respir Crit Care Med.* 163(1):158-165.
Kramer, et al., 2002. Intratracheal endotoxin causes systemic inflammation in ventilated preterm lambs. *Am J Respir Crit Care Med.* 165(4):463-469.
Kuan, et al. 1992. Interactions of surfactant protein D with bacterial lipopolysaccharides. *J. Clin. Invst. The American Society for Clinical Investigation Inc.* 90:97-106.
Kuan, et al., 1991. Interactions of surfactant protein-D with *Escherichia-coli*. *J Cell Biol*. 115(3 Pt 2):236A (Abstract Only).
Kuroki, et al., 1998. Surfactant proteins A and D: disease markers. *Biochim Biophys Acta*. 1408(2-3):334-345.
Lawson, et al., 1999. Genomic organization of the mouse gene for lung surfactant protein D. *Am J Respir Cell Mol Biol*. 20(5):953-963.
Lecuona, et al., 1999. Ventilator-associated lung injury decreases lung ability to clear edema and downregulates alveolar epithelial cell Na,K-adenosine triphosphatase function. *Chest*. 116(1 Suppl):29S-30S.
Leth-Larsen, et al., 2004. Surfactant protein D in the female genital tract. *Mol Hum Reprod*. 10(3):149-154.
LeVine, et al. 1997. Surfactant protein A-deficient mice are susceptible to group B streptococcal infection. *J Immunol*. 158(9): 4336-4340.
LeVine, et al., 1998. Surfactant protein-A-deficient mice are susceptible to Pseudomonas aeruginosa infection. *Am J Respir Cell Mol Biol*. 19(4):700-708.
LeVine, et al., 1999. Surfactant protein-A binds group B *Streptococcus* enhancing phagocytosis and clearance from lungs of surfactant protein-A-deficient mice. *Am J Respir Cell Mol Biol*. 20:279-286.
LeVine, et al., 1999. Surfactant protein-A enhances respiratory syncytial virus clearance in vivo. *J Clin Invest*. 103(7):1015-1021.

LeVine, et al., 2000. Distinct effects of surfactant protein A or D deficiency during bacterial infection on the lung. *J Immunol*. 165(7):3934-3940.
LeVine, et al., 2001. Pulmonary collectins and innate host defense of the lung. *Microbes and Infection*, 3:161-166.
LeVine et al., 2001. Surfactant protein D enhances clearance of influenza A virus from the lung in vivo. J Immunol, 167(10):5868-5873.
LeVine, et al., 2004. Surfactant protein-D enhances phagocytosis and pulmonary clearance of respiratory syncytial virus. *Am J Respir Cell Mol Biol*, 31(2):193-199.
Li, et al., 2002. Microbial infection and inflammation in the development of chronic lung disease of prematurity. *Microbes Infect*. 4(7):723-732.
Lim, et al., 1994. Expression of the carbohydrate recognition domain of lung surfactant protein D and demonstration of its binding to lipopolysaccharides of gram-negative bacteria. *Biochem Biophys Res Commun*. 202(3):1674-1680.
Liu et al., 2002. GATA-6 and thyroid transcription factor-1 directly interact and regulate surfactant protein-C gene expression. J. Biol. Chem. 277(6):4519-4525.
Liu, et al., 2005. Therapeutic effect of surfactant protein D in allergic inflammation of mite-sensitized mice. *Clin Exp Allergy*. 35(4):515-521.
Lowry OH, et al. Protein measurement with the Folin phenol reagent. *J Biol Chem* 1951;193:265-275.
Lu, et al. 1992. Purification, characterization and cDNA cloning of human lung surfactant protein D. *Biochem. J.*, 284:795-802.
Mason, et al. 1998. Surfactant protein A and surfactant protein D in health and disease. Invited Review. *Am J Physiol* 275 (*Lung Cell Mol Physiol* 19) L1-L13.
McCormack; 1995. Molecular biology of the surfactant apoproteins. *Seminars Resp Crit Care Med*. 16(1):29-38.
McIntosh, et al., 1996. Surfactant proteins A and D increase in response to intratracheal lipopolysaccharide. *Am J Respir Cell Mol Biol*.15(4):509-519.
Miyamura, et al. 1994. Surfactant proteins A (SP-A) and D (SP-D): levels in human amniotic fluid and localization in the fetal membranes. Biochim Biophys Acta. 1210(3):303-307.
Motwani, et al., 1995. Mouse surfactant protein-D. cDNA clongin, characterization, and gene localization to chromosome 14. *J Immunol*. 155(12):5671-5677.
Murakami, et al., 2002. Surfactant protein A inhibits peptidoglycan-induced tumor necrosis factor-alpha secretion in U937 and alveolar macrophages by direct interaction with toll-like receptor 2. *J Biol Chem*. 277(9):6830-6837.
Naik AS, et al. Effects of ventilation with different positive end-expiratory pressures on cytokine expression in the preterm lamb lung. *Am J Respir Crit Care Med* 2001;164:494-498.
Naltner, et al., 2000. Retinoic acid stimulation of the human surfactant protein B promoter is thyroid transcription factor 1 site-dependent. J. Biol. Chem. (275(1):56-62.
Ni, et al., 2005. Surfactant protein D is present in human tear fluid and the cornea and inhibits epithelial cell invasion by Pseudomonas aeruginosa. *Infect lmmun*. 73(4):2147-2156.
Noah, et al. 2003. Bronchoalveolar lavage fluid surfactant protein-A and surfactant protein-D are inversely related to inflammation in early cystic fibrosis. *Am J Respir Crit Care Med*. 168(6):685-691.
Norden MA, et al. Predictors of survival for infants with congenital diaphragmatic hernia. *J Pediatr Surg* 1994; 29:1442-1446.
Oberley, et al., 2004. Surfactant protein D is present in the human female reproductive tract and inhibits Chlamydia trachomatis infection. *Mol Hum Reprod*. 10(12):861-870.
Ohya, et al., 2006. Human pulmonary surfactant protein D binds the extracellular domains of Toll-like receptors 2 and 4 . . . *Biochemistry*, 45(28):8657-8664.
Park, et al., 2004. TAZ interacts with TTF-1 and regulates expression of surfactant protein-C. J. Biol. Chem. 279(17):17384-17390.
Pikaar, et al., 1995. Opsonic activities of surfactant proteins A and D in phagocytosis of gram-negative bacteria by alveolar macrophages. *J Infect Dis*. 172(2):481-489.

(56) References Cited

OTHER PUBLICATIONS

Postle, et al. 1999. Deficient hydrophilic lung surfactant proteins A and D with normal surfactant phospholipid molecular species in cystic fibrosis. *Am J Respir Cell Mol Biol*. 20(1):90-98.
Reid; 1998. Functional roles of the lung surfactant proteins SP-A and SP-D in innate immunity. *Immunobiol*., 199:200-207.
Reid; 1998. Interactions of surfactant protein D with pathogens, allergens and phagocytes. *Biochimica et Biophysica Acta*, 1408(2-3):290-295.
Robertson et al. 1998, Principles of surfactant replacement, Biochimica et Biophysica Acta 1408: 346-361.
Sanghavi, et al., 2002. Surfactant protein D levels are increased in tracheal lavage samples from incubated neonates with sepsis. Neonatology; *Pediatr Res*. 51(4 Pt 2):346-347A (Abstract Only).
Sano, et al., 2000. Surfactant proteins A and D bind CD14 by different mechanisms. *J Biol Chem*. 275(29):22442-22451.
Sartori, et al., 2002. Alveolar epithelial fluid transport in acute lung injury: new insights. *Eur Respir J*. 20(5):1299-1313.
Sato, et al., 2003. Direct binding of Toll-like receptor 2 to zymosan, and zymosan-induced NF-Kappa B activation and TNF-alpha secretion are down-regulated by lung collectin surfactant protein A. *J Immunol*. 171(1): 417-425.
Schaub, et al. 2004. Surfactant protein D deficiency influences allergic immune responses. *Clin Exp Allergy*. 34(12):1819-1826.
Schmiedl A, et al. Influence of plasma and inflammatory proteins on the ultrastructure of exogenous surfactant. *J Electron Microsc* (Tokyo) 2004;53:407-416.
Schoel M, et al. The captive bubble method for the evaluation of pulmonary surfactant: surface tension, area, and volume calculations. *Biochim Biophys Acta* 1994;1200:281-290.
Senft, et al., 2005. Surfactant protein-D regulates soluble CD14 through matrix metalloproteinase-12. *J Immunol*. 174(8):4953-4959.
Shapiro SD, et al. Neutrophil elastase contributes to cigarette smoke-induced emphysema in mice. *Am J Pathol* 2003;163:2329-2335.
Shimizu, et al. 1992. Primary structure of rat pulmonary surfactant protein D. *The Journal of Biological Chemistry*, 267(3):1853-1857.
Sorensen, et al. 2006. Genetic and environmental influences of surfactant protein D serum levels. *Am J Physiol Lung Cell Mol Physiol*. 290(5): L1010-L1017.
Sorensen, et al. 2006. Surfactant protein D is proatherogenic in mice. *Am J Physiol Heart Circ Physiol*. 290(6): H2286-H2294.
Stahlman, et al. 2002. Immunolocalization of surfactant protein-D (SP-D) in human fetal, newborn, and adult tissues. *J Histochem Cytochem*. 50(5):651-660.
Strong, et al. 1998. A novel method of purifying lung surfactant proteins A and D from the lung lavage of alveolar proteinosis patients and from pooled amniotic fluid. *J Immunol Methods*. 220(1-2):139-149.
Tokieda, et al., Pulmonary dysfunction in neonatal SP-B deficient mice, Am J Physiol 1997 273:L875-82.
Tryka, et al., 1986. Patterns of cell proliferation during recovery from oxygen injury. Species differences. *Am Rev Respir Dis*. 133(6):1055-1059.
Ueda T, et al. Distribution of surfactant and ventilation in surfactant-treated preterm lambs. *J Appl Physiol* 1994; 76:45-55.
van de Wetering, et al. 2004. Collectins: players of the innate immune system. *Eur J Biochem*. 271(7):1229-1249.
van Eijk, et al., 2000. Porcine lung surfactant protein D: Complementary DNA cloning, chromosomal localization, and tissue distribution. *The Journal of Immunology*, 164(3):1442-1450.
van Iwaarden, et al., 1992. Rat surfactant protein D enhances the production of oxygen radicals by rat alveolar macrophages. *Biochem. J*., 286:5-8.
van Iwaarden, et al., 1994. Binding of surfactant proein A to the lipid A moiety of bacterial lipopolysaccharides. *Biochem J*, 303 (Pt 2):407-411.

van Rozendaal, et al. 1997. Pulmonary surfactant proteins A and D are involved in the early response to intratracheally aerosolized lipopolysaccharide. *Biochem Soc Trans*. 25(4):S656.
van Rozendaal et al. 1999. Aerosolized endotoxin is immediately bound by pulmonary surfactant protein D in vivo. *Biochim Biophys Acta*. 1454(3):261-269.
von Bredow, et al. 2003. Proteolysis of surfactant protein D by cystic fibrosis relevant proteases. *Lung*, 181(2):79-88.
Voorhout, et al., 1992. Immunocytochemical localization of surfactant protein D (SP-D) in type II cells, Clara cells, and alveolar macrophages of rat lung. *J Histochem Cytochem*. 40(10):1589-97.
Vuk-Pavlovic, et al., 2003. Unique chemotypes of *E. coli* LPS exhibit differential interactions with lung surfactant protein-D. *Faseb J*. 17(7):C53 & Enlargement; 2 pages.
Wada K, et al. Tidal volume effects on surfactant treatment responses with the initiation of ventilation in preterm lambs. *J Appl Physiol* 1997;83:1054-1061.
Wan, et al., 2004. Foxa2 is required for transition to air breathing at birth. *Proc. Natl. Acad. Sci. USA* 101(40):14449-14454.
Wan, et al., 2005. Compensatory roles of Foxa1 and Foxa2 during lung morphogenesis. *J. Biol. Chem*. 280(14):13809-13816.
Wang, et al., 1998. Inhibitory effect of pulmonary surfactant proteins A and D on allergen-induced lymphocyte proliferation and histamine release in children with asthma. *Am. J. Respir. Crit. Care Med*., 158:510-518.
Watterberg KL, et al. Secretory leukocyte protease inhibitor and lung inflammation in developing bronchopulmonary dysplasia. *J Pediatr* 1994;125:264-269.
Weirich E, et al. Neutrophil CD11b expression as a diagnostic marker for early-onset neonatal infection. *J Pediatr* 1998; 132:445-451.
Wert, et al. 2000. Increased metalloproteinase activity, oxidant production, and emphysema in surfactant protein D gene-inactivated mice. *PNAS*, 97(11):5972-5977.
Wert, et al., 2002. Increased expression of thyroid transcription factor-1 (TTF-1) in respiratory epithelial cells inhibits alveolarization and causes pulmonary inflammation. *Dev. Biol*. 242(2):75-87.
Whitsett; 2005. Surfactant proteins in innate host defense of the lung. *Biol Neonate*. 88(3):175-180.
Wilson, et al., 2002. Matching SOX: partner proteins and co-factors of the SOX family of transcriptional regulators. *Curr Opin Genet Dev*., 12(4):441-446.
Wright, Immunomodulatory functions of surfactant, Physiological Reviews, 1997, 77:1-32.
Wu, et al., 2003. Surfactant proteins A and D inhibit the growth of Gram-negative bacteria by increasing membrane permeability. *J Clin Invest*. 111(10):1589-1602.
Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006;291:L619-L627).
Yi, et al., 2002. Role of CBP/p300 and SRC-1 in transcriptional regulation of the pulmonary surfactant protein-A (SP-A) gene by thyroid transcription factor-1 (TTF-1). J. Biol. Chem. 277(4):2997-3005.
Yoshida, et al. 2001. Surfactant protein D regulates NF-kappa B and matrix metalloproteinase production in alveolar macrophages via oxidant-sensitive pathways. *Jour. Immunol*., 166(12):7514-7519.
Zhang, et al., 2001. Activity of pulmonary protein-D (SP-D) in vivo is dependent on oligomeric structure. *J Biol Chem*. 276(22):19214-19219.
Zhang, et al., 2002. Reversibility of pulmonary abnormalities by conditional replacement of surfactant protein D (SP-D) in vivo. *J Biol Chem*. 277(41):38709-38713.
Zhou, et al., 1996. Thyroid transcription factor-1, hepatocyte nuclear factor-3beta, surfactant protein B, C, and Clara cell secretory protein in developing mouse lung. J. Histochem. Cytochem. 44(10):1183-1193.

\* cited by examiner

```
                            SEQUENCE LISTING

<160> NUMBER OF SEQ ID NOS: 18

<210> SEQ ID NO 1
<211> LENGTH: 375
<212> TYPE: PRT
<213> ORGANISM: Homo sapien

<400> SEQUENCE: 1

Met Leu Leu Phe Leu Leu Ser Ala Leu Val Leu Leu Thr Gln Pro Leu
 1               5                  10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Leu Pro
        35                  40                  45

Gly Arg Asp Gly Arg Asp Gly Arg Glu Gly Pro Arg Gly Glu Lys Gly
    50                  55                  60

Asp Pro Gly Leu Pro Gly Ala Ala Gly Gln Ala Gly Met Pro Gly Gln
65                  70                  75                  80

Ala Gly Pro Val Gly Pro Lys Gly Asp Asn Gly Ser Val Gly Glu Pro
                85                  90                  95

Gly Pro Lys Gly Asp Thr Gly Pro Ser Gly Pro Pro Gly Pro Pro Gly
            100                 105                 110

Val Pro Gly Pro Ala Gly Arg Glu Gly Pro Leu Gly Lys Gln Gly Asn
        115                 120                 125

Ile Gly Pro Gln Gly Lys Pro Gly Pro Lys Gly Glu Ala Gly Pro Lys
    130                 135                 140

Gly Glu Val Gly Ala Pro Gly Met Gln Gly Ser Ala Gly Ala Arg Gly
145                 150                 155                 160

Leu Ala Gly Pro Lys Gly Glu Arg Gly Val Pro Gly Glu Arg Gly Val
                165                 170                 175

Pro Gly Asn Thr Gly Ala Ala Gly Ser Ala Gly Ala Met Gly Pro Gln
            180                 185                 190

Gly Ser Pro Gly Ala Arg Gly Pro Pro Gly Leu Lys Gly Asp Lys Gly
        195                 200                 205

Ile Pro Gly Asp Lys Gly Ala Lys Gly Glu Ser Gly Leu Pro Asp Val
    210                 215                 220

Ala Ser Leu Arg Gln Gln Val Glu Ala Leu Gln Gly Gln Val Gln His
225                 230                 235                 240

Leu Gln Ala Ala Phe Ser Gln Tyr Lys Lys Val Glu Leu Phe Pro Asn
                245                 250                 255

Gly Gln Ser Val Gly Glu Lys Ile Phe Lys Thr Ala Gly Phe Val Lys
            260                 265                 270

Pro Phe Thr Glu Ala Gln Leu Leu Cys Thr Gln Ala Gly Gly Gln Leu
        275                 280                 285

Ala Ser Pro Arg Ser Ala Ala Glu Asn Ala Ala Leu Gln Gln Leu Val
    290                 295                 300

Val Ala Lys Asn Glu Ala Ala Phe Leu Ser Met Thr Asp Ser Lys Thr
305                 310                 315                 320

Glu Gly Lys Phe Thr Tyr Pro Thr Gly Glu Ser Leu Val Tyr Ser Asn
                325                 330                 335

Trp Ala Pro Gly Glu Pro Asn Asp Asp Gly Gly Ser Glu Asp Cys Val
            340                 345                 350
```

```
Glu Ile Phe Thr Asn Gly Lys Trp Asn Asp Arg Ala Cys Gly Glu Lys
            355                 360                 365

Arg Leu Val Val Cys Glu Phe
    370                 375

<210> SEQ ID NO 2
<211> LENGTH: 355
<212> TYPE: PRT
<213> ORGANISM: Homo sapien

<400> SEQUENCE: 2

Ala Glu Met Lys Thr Tyr Ser His Arg Thr Met Pro Ser Ala Cys Thr
1               5                   10                  15

Leu Val Met Cys Ser Ser Val Glu Ser Gly Leu Pro Gly Arg Asp Gly
                20                  25                  30

Arg Asp Gly Arg Glu Gly Pro Arg Gly Glu Lys Gly Asp Pro Gly Leu
            35                  40                  45

Pro Gly Ala Ala Gly Gln Ala Gly Met Pro Gly Gln Ala Gly Pro Val
    50                  55                  60

Gly Pro Lys Gly Asp Asn Gly Ser Val Gly Glu Pro Gly Pro Lys Gly
65                  70                  75                  80

Asp Thr Gly Pro Ser Gly Pro Pro Gly Pro Pro Gly Val Pro Gly Pro
                85                  90                  95

Ala Gly Arg Glu Gly Pro Leu Gly Lys Gln Gly Asn Ile Gly Pro Gln
            100                 105                 110

Gly Lys Pro Gly Pro Lys Gly Glu Ala Gly Pro Lys Gly Glu Val Gly
    115                 120                 125

Ala Pro Gly Met Gln Gly Ser Ala Gly Ala Arg Gly Leu Ala Gly Pro
    130                 135                 140

Lys Gly Glu Arg Gly Val Pro Gly Glu Arg Gly Val Pro Gly Asn Thr
145                 150                 155                 160

Gly Ala Ala Gly Ser Ala Gly Ala Met Gly Pro Gln Gly Ser Pro Gly
                165                 170                 175

Ala Arg Gly Pro Pro Gly Leu Lys Gly Asp Lys Gly Ile Pro Gly Asp
            180                 185                 190

Lys Gly Ala Lys Gly Glu Ser Gly Leu Pro Asp Val Ala Ser Leu Arg
    195                 200                 205

Gln Gln Val Glu Ala Leu Gln Gly Gln Val Gln His Leu Gln Ala Ala
    210                 215                 220

Phe Ser Gln Tyr Lys Lys Val Glu Leu Phe Pro Asn Gly Gln Ser Val
225                 230                 235                 240

Gly Glu Lys Ile Phe Lys Thr Ala Gly Phe Val Lys Pro Phe Thr Glu
                245                 250                 255

Ala Gln Leu Leu Cys Thr Gln Ala Gly Gly Gln Leu Ala Ser Pro Arg
            260                 265                 270

Ser Ala Ala Glu Asn Ala Ala Leu Gln Gln Leu Val Val Ala Lys Asn
    275                 280                 285

Glu Ala Ala Phe Leu Ser Met Thr Asp Ser Lys Thr Glu Gly Lys Phe
    290                 295                 300

Thr Tyr Pro Thr Gly Glu Ser Leu Val Tyr Ser Asn Trp Ala Pro Gly
305                 310                 315                 320

Glu Pro Asn Asp Asp Gly Gly Ser Glu Asp Cys Val Glu Ile Phe Thr
                325                 330                 335

Asn Gly Lys Trp Asn Asp Arg Ala Cys Gly Glu Lys Arg Leu Val Val
            340                 345                 350
```

Cys Glu Phe
    355

<210> SEQ ID NO 3
<211> LENGTH: 1299
<212> TYPE: DNA
<213> ORGANISM: Homo sapien

<400> SEQUENCE: 3

| | | | | | |
|---|---|---|---|---|---|
| agtttgcttg | gagctcctgg | ggcctaacaa | aaagaaacct | gccatgctgc | tcttcctcct | 60 |
| ctctgcactg | gtcctgctca | cacagcccct | gggctacctg | gaagcagaaa | tgaagaccta | 120 |
| ctcccacaga | acaatgccca | gtgcttgcac | cctggtcatg | tgtagctcag | tggagagtgg | 180 |
| cctgcctggt | cgcgatggac | gggatgggag | agagggccct | cggggcgaga | aggggggaccc | 240 |
| aggtttgcca | ggagctgcag | ggcaagcagg | gatgcctgga | caagctggcc | cagttgggcc | 300 |
| caaaggggac | aatggctctg | ttggagaacc | tggaccaaag | ggagacactg | gccaagtgg | 360 |
| acctccagga | cctcccggtg | tgcctggtcc | agctggaaga | gaaggtcccc | tggggaagca | 420 |
| ggggaacata | ggacctcagg | gcaagccagg | cccaaaagga | gaagctgggc | caaaggagaa | 480 |
| agtaggtgcc | ccaggcatgc | agggctcggc | aggggcaaga | ggcctcgcag | gccctaaggg | 540 |
| agagcgaggt | gtccctggtg | agcgtggagt | ccctggaaac | acaggggcag | cagggtctgc | 600 |
| tggagccatg | ggtccccagg | gaagtccagg | tgccagggga | ccccgggat | tgaaggggga | 660 |
| caaaggcatt | cctggagaca | aggagcaaa | gggagaaagt | gggcttccag | atgttgcttc | 720 |
| tctgaggcag | caggttgagg | ccttacaggg | acaagtacag | cacctccagg | ctgctttctc | 780 |
| tcagtataag | aaagttgagc | tcttcccaaa | tggccaaagt | gtcggggaga | agattttcaa | 840 |
| gacagcaggc | tttgtaaaac | catttacgga | ggcacagctg | ctgtgcacac | aggctggtgg | 900 |
| acagttggcc | tctccacgct | ctgccgctga | aatgccgcc | ttgcaacagc | tggtcgtagc | 960 |
| taagaacgag | gctgctttcc | tgagcatgac | tgattccaag | acagagggca | agttcaccta | 1020 |
| ccccacagga | gagtccctgg | tctattccaa | ctgggcccca | ggggagccca | acgatgatgg | 1080 |
| cgggtcagag | gactgtgtgg | agatcttcac | caatggcaag | tggaatgaca | gggcttgtgg | 1140 |
| agaaaagcgt | cttgtggtct | gcgagttctg | agccaactgg | ggtgggtggg | gcagtgcttg | 1200 |
| gcccaggagt | ttggccagaa | gtcaaggctt | agaccctcat | gctgccaata | tcctaataaa | 1260 |
| aaggtgacca | tctgtgccgg | gaaaaaaaaa | aaaaaaaaa | | | 1299 |

<210> SEQ ID NO 4
<211> LENGTH: 1221
<212> TYPE: DNA
<213> ORGANISM: Homo sapien

<400> SEQUENCE: 4

| | | | | | |
|---|---|---|---|---|---|
| gcgaattcaa | acctgccatg | ctgctcttcc | tcctctctgc | actggtcctg | ctcacacagc | 60 |
| ccctgggcta | cctggaagca | gaaatgaaga | cctactccca | cagaacaatg | cccagtgctt | 120 |
| gcaccctggt | catgtgtagc | tcagtggaga | gtggcctgcc | tggtcgcgat | ggacgggatg | 180 |
| ggagagaggg | ccctcggggc | gagaaggggg | acccaggttt | gccaggagct | gcagggcaag | 240 |
| cagggatgcc | tggacaagct | ggcccagttg | ggcccaaagg | ggacaatggc | tctgttggag | 300 |
| aacctggacc | aaagggagac | actgggccaa | gtggacctcc | aggacctccc | ggtgtgcctg | 360 |
| gtccagctgg | aagagaaggt | ccctgggga | agcaggggaa | cataggacct | cagggcaagc | 420 |
| caggcccaaa | aggagaagct | gggcccaaag | gagaagtagg | tgccccaggc | atgcagggct | 480 |

```
cggcagggc  aagaggcctc  gcaggccta  agggagagcg  aggtgtccct  ggtgagcgtg    540
gagtccctgg  aaacacaggg  gcagcagggt  ctgctggagc  catgggtccc  cagggaagtc    600
caggtgccag  ggaccccg   ggattgaagg  gggacaaagg  cattcctgga  gacaaaggag    660
caaagggaga  aagtgggctt  ccagatgttg  cttctctgag  gcagcaggtt  gaggccttac    720
agggacaagt  acagcacctc  caggctgctt  tctctcagta  taagaaagtt  gagctcttcc    780
caaatggcca  aagtgtcggg  gagaagattt  tcaagacagc  aggctttgta  aaaccattta    840
cggaggcaca  gctgctgtgc  acacaggctg  gtggacagtt  ggcctctcca  cgctctgccg    900
ctgagaatgc  cgccttgcaa  cagctggtcg  tagctaagaa  cgaggctgct  ttcctgagca    960
tgactgattc  caagacagag  ggcaagttca  cctaccccac  aggagagtcc  ctggtctatt   1020
ccaactgggc  cccaggggag  cccaacgatg  atggcgggtc  agaggactgt  gtggagatct   1080
tcaccaatgg  caagtggaat  gacagggctt  gtggagaaaa  gcgtcttgtg  gtctgcgagt   1140
tctgagccaa  ctggggtggg  tgggcagtg  cttggcccag  gagtttggcc  agaagtcaag   1200
gcttagaccc  tcaggatcct  c                                                1221

<210> SEQ ID NO 5
<211> LENGTH: 20
<212> TYPE: DNA
<213> ORGANISM: Ovis aries

<400> SEQUENCE: 5
tggccaggat tcacgagttc                                                      20

<210> SEQ ID NO 6
<211> LENGTH: 30
<212> TYPE: DNA
<213> ORGANISM: Ovis aries

<400> SEQUENCE: 6
tctgtgaggt agaaagatga ctgagatatt                                           30

<210> SEQ ID NO 7
<211> LENGTH: 25
<212> TYPE: DNA
<213> ORGANISM: Ovis aries

<400> SEQUENCE: 7
ggaggaaaaa gatggatgct tccaa                                                25

<210> SEQ ID NO 8
<211> LENGTH: 23
<212> TYPE: DNA
<213> ORGANISM: Ovis aries

<400> SEQUENCE: 8
cagcagtggt tttgatcaag caa                                                  23

<210> SEQ ID NO 9
<211> LENGTH: 19
<212> TYPE: DNA
<213> ORGANISM: Ovis aries

<400> SEQUENCE: 9
ggctctccac ctcctctca                                                       19

<210> SEQ ID NO 10
```

```
<211> LENGTH: 19
<212> TYPE: DNA
<213> ORGANISM: Ovis aries

<400> SEQUENCE: 10
agctcatgca gaacacctt                                                    19

<210> SEQ ID NO 11
<211> LENGTH: 21
<212> TYPE: DNA
<213> ORGANISM: Ovis aries

<400> SEQUENCE: 11
gccggaatac ctggactatg c                                                 21

<210> SEQ ID NO 12
<211> LENGTH: 22
<212> TYPE: DNA
<213> ORGANISM: Ovis aries

<400> SEQUENCE: 12
cagggcgatg atcccaaagt ag                                                22

<210> SEQ ID NO 13
<211> LENGTH: 17
<212> TYPE: DNA
<213> ORGANISM: Ovis aries

<400> SEQUENCE: 13
tgccagtgcc tgcagac                                                      17

<210> SEQ ID NO 14
<211> LENGTH: 22
<212> TYPE: DNA
<213> ORGANISM: Ovis aries

<400> SEQUENCE: 14
agtggctatg acttcggttt gg                                                22

<210> SEQ ID NO 15
<211> LENGTH: 23
<212> TYPE: DNA
<213> ORGANISM: Ovis aries

<400> SEQUENCE: 15
ccccgactat ctgtttccac aac                                               23

<210> SEQ ID NO 16
<211> LENGTH: 21
<212> TYPE: DNA
<213> ORGANISM: Ovis aries

<400> SEQUENCE: 16
cctggaaggg cttctgatct g                                                 21

<210> SEQ ID NO 17
<211> LENGTH: 23
<212> TYPE: DNA
<213> ORGANISM: Ovis aries

<400> SEQUENCE: 17
gcagaagatt caagggccag atc                                               23
```

```
<210> SEQ ID NO 18
<211> LENGTH: 23
<212> TYPE: DNA
<213> ORGANISM: Ovis aries

<400> SEQUENCE: 18
ggttttcttg ttgctcccgt aac                                              23
```

SURFACTANT PROTEIN D FOR THE TREATMENT OF DISORDERS ASSOCIATED WITH LUNG INJURY

CROSS-REFERENCE TO RELATED APPLICATIONS

This application is a continuation of U.S. application Ser. No. 14/062,682 filed on Oct. 24, 2013, now U.S. Pat. No. 9,492,503 which is a continuation of U.S. application Ser. No. 13/366,144 filed on Feb. 3, 2012 which claims priority to U.S. Provisional Application Ser. No. 61/439,760, filed on Feb. 4, 2011, which are incorporated herein by reference in their entireties.

STATEMENT REGARDING FEDERALLY SPONSORED R&D

This invention was made with government support under HL085610 awarded by the National Institutes of Health. The government has certain rights in the invention.

REFERENCE TO SEQUENCE LISTING

The present application is being filed along with a Sequence Listing in electronic format. The Sequence Listing is provided as a file entitled AIRWY003C2SEQLIST, created Nov. 1, 2016, which is about 12 KB in size. The information in the electronic format of the Sequence Listing is incorporated herein by reference in its entirety.

BACKGROUND

Surfactant protein D (SP-D) is a member of the collectin family of collagenous lectin domain-containing proteins that is expressed in epithelial cells of the lung.

SUMMARY OF THE INVENTION

Described herein are methods and compositions for the treatment of disorders associated with lung injury, including methods and compositions for the treatment of bronchopulmonary disorder (BPD).

In one embodiment, a method for reducing the risk of developing bronchopulmonary dysplasia (BPD) is provided, comprising administering a composition comprising recombinant human SP-D (rhSP-D) and a pulmonary surfactant to a subject in need thereof in an amount effective to reduce the risk of developing BPD. In some aspects, the BPD is associated with lung injury from mechanical ventilation. In some aspects, the composition further comprises at least one protein selected from the group consisting of surfactant protein A (SP-A), surfactant protein B (SP-B), surfactant protein C (SP-C), and fragments and mimics thereof. In some aspects, the pulmonary surfactant is a synthetic surfactant protein. In some aspects, the dose of the rhSP-D is about 0.1 mg to about 10 mg/kg body weight of the subject. In some aspects, the dose of the rhSP-D is about 2 mg/kg body weight. In some aspects, the total dose of the composition is about 100 mg/kg body weight of the subject. In some aspects, the composition is administered intratracheally. In some aspects, the method further comprises selecting a subject at risk for developing BPD prior to administering the composition to the subject. In some aspects, the subject is an infant.

In another embodiment, a method of reducing pulmonary injury associated with ventilation in a subject is provided, comprising administering recombinant human surfactant protein D (rhSP-D) and a pulmonary surfactant to the subject in an amount effective to reduce pulmonary injury associated with the ventilation. In some aspects, the ventilation is mechanical ventilation. In some aspects, the composition further comprises at least one protein selected from the group consisting of surfactant protein A (SP-A), surfactant protein B (SP-B), surfactant protein C (SP-C), and fragments and mimics thereof. In some aspects, the pulmonary surfactant is a synthetic surfactant protein. In some aspects, the dose of the rhSP-D is about 0.1 mg to about 10 mg/kg body weight of the subject. In some aspects, the dose of the rhSP-D is about 2 mg/kg body weight of the subject. In some aspects, the total dose of the composition is about 100 mg/kg body weight of the subject. In some aspects, the composition is introduced intratracheally. In some aspects, the method further comprises selecting a subject at risk for developing BPD prior to administering the composition to the subject. In some aspects, the subject is an infant.

DETAILED DESCRIPTION OF THE INVENTION

Figure 1:
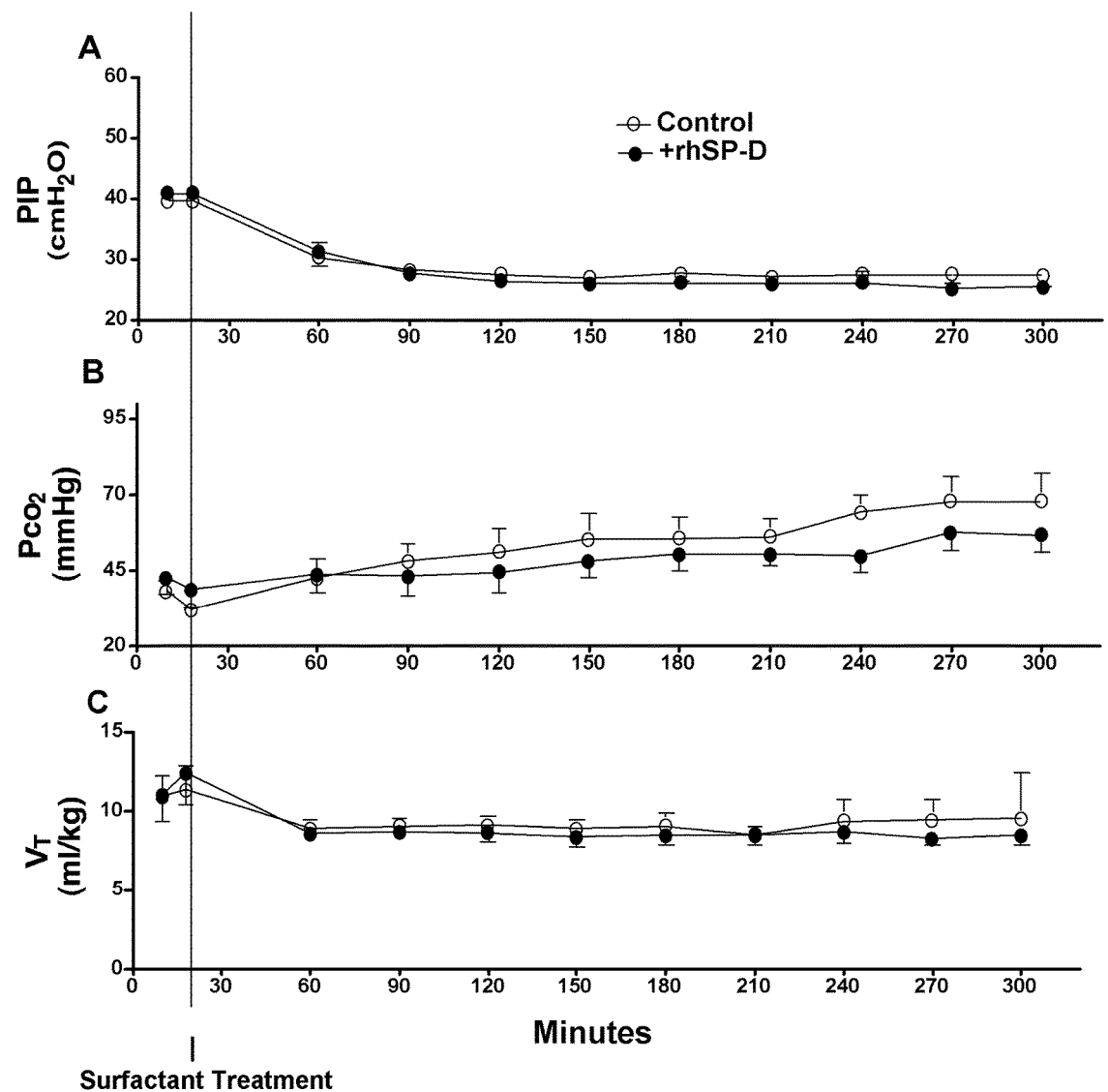
FIG. 1 shows that treatment with recombinant human surfactant protein D (rhSP-D) does not alter lung physiology in premature lambs. Premature newborn lambs were resuscitated after birth by ventilation with a peak inspiratory pressure (PIP) of $H_2O$, resulting in a mean $P\text{co}_2$ of 40 mm Hg (B) and a mean $V_T$ of 11 ml/kg (C) for rhSP-D treated lambs and controls. Surfactant was given at 20 minutes of age and ventilation was changed to regulate $V_T$ at 8 to 9 ml/kg (C), requiring a mean PIP of 27 cm $H_2O$ (A) for rhSP-D treated lambs and controls.

Premature newborns are routinely resuscitated by manual ventilation in the delivery room, followed by mechanical ventilation and surfactant treatment in the neonatal intensive care unit. The premature lung requires high inflating pressures and oxygen for adequate ventilation and oxygenation and is highly susceptible to injury because of its structural immaturity, surfactant deficiency, presence of fetal lung fluid, and immature immune system—factors that are likely to contribute to the development of the chronic lung disease bronchopulmonary dysplasia (BPD). Surfactant treatment is routinely given to very low birth weight (i.e., <1,500 g) preterm infants as early as possible after birth for the purpose of resuscitation in an effort to prevent and/or treat neonatal respiratory distress.

As described herein, rhSP-D can be added to resuscitation surfactant to improve surfactant distribution, minimize inhibition of surfactant function by leaked proteins, and prevent bronchopulmonary dysplasia (BPD)—a frequent consequence of the resuscitation process. Some embodiments relate to methods and compositions for the treatment of disorders associated with lung injury, including BPD. In one embodiment, recombinant human surfactant protein D (rhSP-D) is given in combination with a surfactant formulation to a mammal in need of treatment for a lung disorder. In some embodiments, the methods described herein reduce the risk of developing BPD. In some embodiments, the methods described herein reduce pulmonary injury associated with ventilation. In some embodiments, the methods described herein reduce pulmonary injury associated with the administration of oxygen, including high levels of oxygen. In some embodiments, the methods described herein reduce pulmonary injury associated with infection, such as intra-uterine infection.

In some embodiments, the mammal is a human. The human can be, e.g., an adult, a child, or an infant. In some embodiments, the infant is a newborn infant or a premature newborn infant. In some embodiments, the premature newborn infant is born at about 21, 22, 23, 24, 25, 26, 27, 28, 29, 30, 31, 32, 33, 34, 35, 36, or 37 weeks gestational age. In some embodiments, the newborn infant has a low birth weight. For example, in some embodiments, the birth weight of the newborn infant is less than about 500, 600, 700, 800, 900, 1000, 1100, 1200, 1300, 1400, 1500, 1600, 1700, 1800, 1900, 2000, 2100, 2200, 2300, 2400, or 2500 grams. In a preferred embodiment, the mammal is a premature newborn infant with respiratory disease (such as neonatal respiratory distress syndrome (nRDS)), or an infant at risk of developing or with symptoms of BPD.

In the embodiments described herein, a surfactant formulation can encompass one or more proteins, protein fragments, or mimics thereof. For example, in some embodiments, the surfactant formulation contains surfactant protein A (SP-A), and/or surfactant protein B (SP-B), and/or surfactant protein C (SP-C). In some embodiments, the surfactant formulation contains a combination of surfactant proteins, such as the combination of SP-B and SP-C. In some embodiments, the surfactant formulation contains a fragment of a surfactant protein. In some embodiments, the surfactant formulation contains lipids. For example, in some embodiments, the surfactant formulation contains dipalmitoylphosphatidylcholine (DPPC). In some embodiments, the formulation contains DPPC and at least one of phosphatidylglycerol (PG) and phosphatidylinositol (PI). In a preferred embodiment, the surfactant formulation contains SP-B, SP-C, and DPPC.

In some embodiments, the surfactant formulation contains an animal derived surfactant. In some embodiments, the animal derived surfactant is a commercially available surfactant, such as ALVEOFACT®, CUROSURF®, INFASURF®, or SURVANTA®. In some embodiments, the animal derived surfactant is BLES®, SURFACEN®, or CLSE®. In some embodiments, the surfactant formulation contains a synthetic surfactant. In some embodiments, the synthetic surfactant is a commercially available synthetic surfactant, such as EXOSURF®, PUMACTANT®, SURFAXIN®, AEROSURF®, VENTICUTE®, or CHF 5633. In some embodiments, a combination treatment of rhSP-D and an animal surfactant is provided. In some of these embodiments, the animal surfactant contains at least one surfactant protein and at least one lipid. In some embodiments, a combination treatment of rhSP-D and a synthetic surfactant is provided. In some of these embodiments, the synthetic surfactant contains at least one recombinant protein, at least one surfactant protein fragment or mimic of a surfactant protein, and at least one lipid.

In some embodiments, the surfactant formulation contains a purified surfactant protein. In some embodiments, the surfactant formulation contains a recombinant protein. In some embodiments, the surfactant formulation contains a surfactant protein that is not SP-D. In some embodiments, the surfactant formulation does not contain a surfactant protein. In some embodiments, the surfactant formulation contains a lipoprotein complex. For example, in some embodiments, the surfactant formulation contains a phospholipoprotein complex.

The compositions described herein can be administered by any suitable route, including orally, intratracheally, parenterally, by inhalation spray, rectally, or topically in dosage unit formulations containing conventional pharmaceutically acceptable carriers, adjuvants, and vehicles. As used herein, the term "parenteral" includes subcutaneous, intravenous, intraarterial, intramuscular, intrasternal, intratendinous, intraspinal, intracranial, intrathoracic, infusion, or intraperitoneal administration. In a preferred embodiment, a composition described herein is administered intratracheally. In another preferred embodiment, a composition described herein is administered in an aerosolized form. For example, in one embodiment, rhSP-D and a surfactant formulation are administered as an aerosolized product that is administered by mask or continuous positive airway pressure (CPAP).

The compositions described herein can be administered as a single dose or in multiple doses. In some embodiments, the composition is administered once. In some embodiments, the composition is administered more than once. In a preferred embodiment, the composition is administered to a premature newborn infant in one or two doses. In some embodiments, rhSP-D and a surfactant formulation are each administered once per day. In some embodiments, rhSP-D and a surfactant formulation are administered together once per day. In some embodiments, rhSP-D and a surfactant formulation are administered together more than once per day.

In some embodiments, one or both of rhSP-D and a surfactant formulation is administered one, two, three, four, or more times per day. However, either or both can be administered less than once per day, e.g., about once every 2, 3, 4, 5, 6, 7, 8, 9, 10, 11, 12, 13, or 14 days.

Suitable dose ranges vary, but in general, the rhSP-D can be administered in a dose of about 0.1, 0.2, 0.3, 0.4, 0.5, 0.6, 0.7, 0.8, 0.9, 1, 2, 3, 4, 5, 6, 7, 8, 9, or 10 mg/kg body weight. In a preferred embodiment, the rhSP-D is provided in a dose of about 1 mg/kg to about 2 mg/kg body weight. In general, the surfactant formulation can be administered in a dose of about 25, 50, 75, 100, 125, 150, 175, 200, 300, 400, or 500 mg/kg body weight. In a preferred embodiment, the surfactant formulation is provided in a dose of about 100 mg/kg to about 200 mg/kg body weight. For example, in a preferred embodiment, the rhSP-D is provided in a dose of about 2 mg/kg body weight, and the surfactant formulation is provided in a dose of about 100 mg/kg body weight. In another preferred embodiment, the rhSP-D is provided in a dose of about 7 mg/kg body weight, and the surfactant formulation is provided in a dose of about 100 mg/kg body weight. In some embodiments, the dose of rhSP-D is about 0.25%, 0.5%, 0.75%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, or 5% of the total dose of a composition. For example, in a preferred embodiment, the dose of rhSP-D is 2 mg/kg body weight in a total dose of 100 mg/kg body weight (i.e., 2%) of rhSP-D and a surfactant formulation.

The selection of a particular dose may be based on the weight or identity of a mammal, the dose, and/or the dosing schedule of another co-administered compound. However, in some embodiments, it may be necessary to use doses outside the ranges described above. In some embodiments, the daily dosage of rhSP-D and a surfactant formulation are the same, and in some embodiments, the daily dosages vary. In some embodiments, the rhSP-D and surfactant formulation are administered together. In some embodiments, the rhSP-D and surfactant formulation are administered separately. In some embodiments, the daily dosage of a composition described herein is administered in a single dosage form. In some embodiments, the daily dosage of a composition described herein is administered in multiple dosage forms.

In some embodiments, at least one of rhSP-D and a surfactant formulation is administered in consistent daily dosages throughout the period of treatment. In some embodiments, at least one of rhSP-D and a surfactant formulation is administered in varying daily dosages during the period of treatment. In some of these embodiments, the daily dosages comprise increasing daily dosages over time.

In some of these embodiments, the daily dosages comprise decreasing daily dosages over time.

In some embodiments, the dosage is adjusted so that the mammal maintains or exhibits reduced symptoms of a disorder. For example, in some embodiments, the dosage is adjusted so that a patient exhibits a reduction in symptoms of BPD. However, the dosage may also be adjusted by a treating physician based on a patient's particular needs. Further, the exact formulation, route of administration, and dosage can be chosen by a physician in view of the patient's condition.

In some embodiments, at least one of rhSP-D and a surfactant formulation is administered with varying frequency during treatment. In some of these embodiments, the varying frequency comprises a decreased frequency over time. For example, one or both of rhSP-D and the surfactant formulation can be initially administered more than once per day, followed by administration only once per day at a later point in treatment. In some embodiments, the daily dosage of at least one of rhSP-D and a surfactant formulation is consistent despite the varying frequency of administration.

In some embodiments, rhSP-D and a surfactant formulation are administered in a single pharmaceutical composition, such as a pharmaceutical composition comprising rhSP-D, a purified surfactant protein, a lipid, and a pharmaceutically acceptable carrier.

In some embodiments, administration is continued for a certain amount of time or until a particular outcome is achieved. For example, in some embodiments, administration of the compositions provided herein is continued for a period of at least about 1, 2, 3, 4, 5, 6, 7, 8, 9, 10, 11, 12, 16, 20, 24, 36, 48, 72, 84, 96, 108, or 120 hours. In some embodiments, administration of rhSP-D and a surfactant formulation is continued until the reduction in symptoms of respiratory distress is stabilized for a period of at least about 12, 16, 20, 24, 36, 48, 72, 84, 96, 108, or 120 hours. In a preferred embodiment, symptoms of respiratory distress are stabilized for a period of about 72 hours to about 96 hours. In some embodiments, administration is continued for the duration of the life of a mammal. For example, in some embodiments, administration is continued daily, weekly, or monthly for the life of a human.

The compositions described herein may be accompanied by instructions for administration. Such notice, for example, may be the labeling approved by the U.S. Food and Drug Administration for prescription drugs, or an approved product insert. Compositions formulated in a compatible pharmaceutical carrier may also be prepared, placed in an appropriate container, and labeled for treatment of an indicated condition.

Instructions and/or information may be present in a variety of forms, including printed information on a suitable medium or substrate (e.g., a piece or pieces of paper on which the information is printed), computer readable medium (e.g., diskette, CD, etc., on which the information has been recorded), or a website address that may be accessed via the internet. Printed information may, for example, be provided on a label associated with a drug product, on the container for a drug product, packaged with a drug product, or separately provided apart from a drug product, or provided in a manner in which a patient can independently obtain the information (e.g., a website). Printed information may also be provided to a medical caregiver involved in treatment of a patient.

The compositions described herein can be provided prior to, simultaneously with, or subsequent to ventilation and/or oxygen treatment. In some embodiments, the mammal receives ventilation and/or oxygen treatment for a period of time prior to receiving a composition. For example, in some embodiments, the mammal receives ventilation and/or oxygen treatment for about 1, 2, 3, 4, 5, 10, 15, 20, 25, 30, 35, 40, 45, 50, 55, 60, 75, 90, 105, or 120 minutes prior to receiving a composition. In some embodiments, the mammal receives ventilation and/or oxygen treatment for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours prior to receiving a composition. In a preferred embodiment, a premature infant receives ventilation immediately following birth, and treatment with rhSP-D and a surfactant formulation within about 20 minutes of birth. For example, a premature infant can be intubated with an endotracheal tube and placed on a ventilator at birth, then receive rhSP-D and a surfactant formulation through the endotracheal tube about 20 minutes following birth. In some embodiments, the ventilation is manual ventilation. In some embodiments, the ventilation is mechanical ventilation. In some embodiments, the ventilation is both manual and mechanical. For example, in some embodiments, a premature infant is resuscitated by manual ventilation in the delivery room, followed by mechanical ventilation and treatment with rhSP-D and a surfactant formulation in the neonatal intensive care unit. In some embodiments, the mammal receives a composition about 1, 2, 3, 4, 5, 10, 15, 20, 25, 30, 35, 40, 45, 50, 55, 60, 75, 90, 105, or 120 minutes prior to ventilation and/or oxygen treatment for a lung disorder. In some embodiments, the mammal receives a composition about 1, 2, 3, 4, 5, 6, 7, 8, 9, 10, 11, 12, 13, 14, 15, 16, 17, 18, 19, 20, 21, 22, 23, or 24 hours prior to treatment for a lung disorder. For example, in some embodiments, a patient with cystic fibrosis receives a composition within an hour of undergoing ventilation treatment. However, this timeframe can be adjusted by a treating physician based on a patient's particular needs.

In some embodiments, the mammal receives alternating treatment with a composition and ventilation and/or oxygen. For example, in some embodiments, the mammal receives ventilation, followed by a composition, followed by ventilation. In some embodiments, the mammal receives alternating and simultaneous treatment with a composition and ventilation and/or oxygen. For example, in some embodiments, the mammal receives a composition, followed by ventilation, followed by the composition and ventilation.

In some embodiments, the mammal is administered a composition described herein within a defined period of time following birth. In some embodiments, the mammal is administered a composition immediately following birth. In some embodiments, the mammal is administered a composition within about 1, 2, 3, 4, 5, 6, 7, 8, 9, 10, 15, 20, 25, 30, 35, 40, 45, 50, 55, 60, 75, 90, 105, or 120 minutes of birth.

The term "treatment" can include any intervention performed with the intention of preventing the development or altering the pathology of a disorder. Accordingly, "treatment" refers to both therapeutic treatment and prophylactic or preventative measures. Those in need of treatment include those already with a disorder, as well as those in which the disorder is to be prevented. In some embodiments, the compositions described herein are useful to reduce the risk of developing BPD. In some embodiments, the compositions described herein are useful for reducing pulmonary inflammation associated with lung injury. In some embodiments, the compositions described herein are useful for reducing the symptoms of BPD resulting from lung injury.

The terms "protein," "polypeptide," and "peptide" are used interchangeably herein to refer to a polymer of amino acid residues. The terms can apply to amino acid polymers in which one or more amino acid residue is an analog or mimic of a corresponding naturally occurring amino acid, as well as to naturally occurring amino acid polymers. Polypeptides can be produced via several methods known in the art. For example, polypeptide products can be biochemically synthesized by employing standard solid phase techniques. Such methods include, but are not limited to, exclusive solid phase synthesis, partial solid phase synthesis methods, fragment condensation, and classical solution syntheses known to those of skill in the art. Polypeptides can also be generated using recombinant techniques known to those of skill in the art. For example, polypeptides can be synthesized by cloning a polynucleotide comprising the cDNA of a gene into an expression vector and culturing the cell harboring the vector to express the encoded polypeptide. In addition, polypeptides can be purified using methods known to those of skill in the art, including preparative high performance liquid chromatography. As used herein, the term "purified" does not require absolute purity; rather, it is intended as a relative definition. In some embodiments, a polypeptide is about 75%, 80%, 85%, 90%, 95%, or 99% pure. Polypeptides can also be modified, e.g., by the addition of carbohydrate residues to form glycoproteins. The terms "protein," "polypeptide," and "peptide" include glycoproteins, as well as non-glycoproteins.

In some embodiments, the rhSP-D has the amino acid sequence of SEQ ID NO: 1. In some embodiments, the rhSP-D has an amino acid sequence that is at least 75%, 80%, 85%, 90%, 91%, 92%, 93%, 94%, 95%, 96%, 97%, 98%, or 99% identical to SEQ ID NO: 1. In some embodiments, the rhSP-D comprises the amino acid sequence of SEQ ID NO: 2 (NP_003010.4). In some embodiments, the rhSP-D comprises an amino acid sequence that is at least 75%, 80%, 85%, 90%, 91%, 92%, 93%, 94%, 95%, 96%, 97%, 98%, or 99% identical to SEQ ID NO: 2 (precursor sequence of NP_003010.4). In some embodiments, the rhSP-D is encoded by the nucleic acid sequence of SEQ ID NO: 3 (NM_003019). In some embodiments, the rhSP-D is encoded by a nucleic acid sequence that is at least 75%, 80%, 85%, 90%, 91%, 92%, 93%, 94%, 95%, 96%, 97%, 98%, or 99% identical to SEQ ID NO: 3. In some embodiments, the rhSP-D is expressed from a vector containing the nucleic acid sequence of SEQ ID NO: 4. In some embodiments, the rhSP-D is expressed from a vector containing a nucleic acid sequence that is at least 75%, 80%, 85%, 90%, 91%, 92%, 93%, 94%, 95%, 96%, 97%, 98%, or 99% identical to SEQ ID NO: 4. As will be appreciated by one of skill in the art, particular motifs and the degree of conservation between species provides guidance as to areas of rhSP-D that are important for structure and function (and are therefore not good candidates for varying from the sequences provided herein), and areas of variation that do not need to be conserved in the same manner.

The compositions described herein can include pharmaceutically acceptable carriers, such as adjuvants, excipients, and/or stabilizers that are nontoxic to the cell or mammal being exposed thereto at the doses and concentrations employed. In some embodiments, the pharmaceutically acceptable carrier is an aqueous pH buffered solution. For example, in some embodiments, compositions are pH adjusted with sodium bicarbonate. Examples of pharmaceutically acceptable carriers include, but are not limited to, adjuvants, lipids, preservatives, stabilizers, wetting agents, emulsifiers, and buffers. In some embodiments, the compositions contain a lipid. For example, in some embodiments, the compositions contain phosphatidylcholine (PC), dipalmitoylphosphatidylcholine (DPPC), phosphatidylglycerol (PG), phosphatidylethanolamine (PE), phosphatidylinositol (PI), sphingomyelin, tripalmitoylglycerol, palmitic acid, or mixtures thereof, In a preferred embodiment, compositions contain a rhSP-D, a surfactant protein, DPPC, and PI. Further, compositions can be prepared in solid form (including granules, powders or suppositories) or liquid form (e.g., solutions, suspensions, or emulsions). For example, in some embodiments, compositions are suspended in sodium chloride solution. In a preferred embodiment, the composition is in an aerosolized formulation.

EXAMPLE 1 rhSP-D Treatment in Premature Lambs

Premature lambs were delivered by cesarean section at 130 days' gestational age (GA) (full term is 150 days GA) and tracheostomized as previously described (Kramer B W, et al. Surfactant protein A recruits neutrophils into the lungs of ventilated pretemi lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). Premature newborn lambs were resuscitated with 100% $O_2$, a peak inspiratory pressure (PIP) of 40 cm $H_2O$, 4 cm $H_2O$ positive end-expiratory pressure (PEEP), and a respiratory rate of 40/min using a pressure-limited ventilator (Sechrist Industries, Anaheim, Calif.). To avoid overstretch of the premature newborn infant lung during manual ventilation, the clinical resuscitation bag has a pressure relief valve set at 40 cm $H_2O$, and therefore PIP for resuscitation was limited to 40 cm $H_2O$.

Premature lambs at 130 days GA require surfactant treatment to survive. At 20 minutes of age, two groups of lambs were treated with SURVANTA® (Abbott Laboratories, Columbus, Ohio) mixed with rhSP-D (SEQ ID NO: 1) (+rhSP-D group) or buffer (control group) using two boluses for instillation (Ueda T, et al. Distribution of surfactant and ventilation in surfactant-treated preterm lambs. *J Appl Physiol* 1994; 76:45-55). rhSP-D was synthesized as previously described (Ikegami M, et al. Intratracheal recombinant surfactant protein D prevents endotoxin shock in the newborn preterm lamb. *Am J Respir Crit Care Med* 2006; 173:1342-1347; Ikegami M, et al. Surfactant protein-D and surfactant inhibit endotoxin induced pulmonary inflammation. *Chest* 2007; 132:1447-1454; Ikegami M, et al. Surfactant protein-D regulates the postnatal maturation of pulmonary surfactant lipid pool sizes. *J Appl Physiol* 2009; 106: 1545-1552). Seven milligrams of rhSP-D in 5 ml buffer (20 mM Tris, 200 mM NaCl, 1 mM ethylenediaminetetraacetic acid, pH 7.4) or 5 ml buffer alone were mixed with a clinical treatment dose of SURVANTA® (100 mg/4 ml/kg)—amounts that are similar to both SP-D and surfactant lipid pool sizes in the normal term newborn lung (Ikegami M, et al. Surfactant protein-D regulates the postnatal maturation of pulmonary surfactant lipid pool sizes. *J Appl Physiol* 2009; 106:1545-1552; Ikegami M, Jobe A H. Surfactant metabolism. *Semin Perinatol* 1993; 17:233-240). After surfactant treatment, the PIP was decreased to regulate tidal volume ($V_T$) at 8 to 9 ml/kg (Bicore Monitoring Systems, Anaheim, Calif.), and $F_{iO2}$ was adjusted to maintain a target $P_{O2}$ of 100 to 150 mm Hg. Ventilatory rate, inspiratory time of 0.6 seconds, and PEEP were not changed.

A five hour study period was chosen to detect changes in proinflammatory cytokine mRNAs induced by initial ventilation (Naik A S, et al. Effects of ventilation with different positive end-expiratory pressures on cytokine expression in the preterm lamb lung. *Am J Respir Crit Care Med* 2001; 164:494-498). After five hours, lambs were ventilated with $F_{iO2}$=1 for five minutes, then given 100 mg pentobarbital intravascularly, after which the endotracheal tube was clamped to permit oxygen absorption atelectasis (Ikegami M, et al. Intratracheal recombinant surfactant protein D prevents endotoxin shock in the newborn preterm lamb. *Am J Respir Crit Care Med* 2006; 173:1342-1347; Ikegami M, Jobe A. Postnatal lung inflammation increased by ventilation of preterm lambs exposed antenatally to *E. coli* endotoxin. *Pediatr Res* 2002; 52:356-362). After the thorax was opened, the deflation limb of pressure-volume curve was measured (Kramer B W, et al. Surfactant protein A recruits neutrophils into the lungs of ventilated preterm lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). Lung tissue of the right lower lobe was frozen in liquid nitrogen for RNA isolation and measurement of neutrophil elastase (NE) activity (Lowry O H, et al. Protein measurement with the Folin phenol reagent. *J Biol Chem* 1951; 193:265-275; Watterberg K L, et al. Secretory leukocyte protease inhibitor and lung inflammation in developing bronchopulmonary dysplasia. *J Pediatr* 1994; 125:264-269). NE is a potent serine proteinase, responsible for tissue destruction in the adult lung with emphysema (Shapiro S D, et al. Neutrophil elastase contributes to cigarette smoke-induced emphysema in mice. *Am J Pathol* 2003; 163:2329-2335). In the preterm newborn lung, increased NE activity affects lung remodeling and increases alveolar epithelial apoptosis and the development of BPD (Watterberg K L, et al. Secretory leukocyte protease inhibitor and lung inflammation in developing bronchopulmonary dysplasia. *J Pediatr* 1994; 125:264-269; Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627). NE activity was assessed by a spectrophotometric assay using a chromogenic substrate specific for NE, N-methoxy-succinyl-Ala-Ala-Pro-Val pNA (Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627).

Sequences of primers for quantitative reverse transcriptase-polymerase chain reaction were: IL-8: 5'-TGGCCAGGATTCACGAGTTC (SEQ ID NO:5) and 5'-TCTGTGAGGTAGAAAGATGACTGAGATATT (SEQ ID NO:6); IL-6: 5'-GGAGGAAAAAGATGGATGCTTCCAA (SEQ ID NO:7) and 5'-CAGCAGTGGTTTTGATCAAGCAA (SEQ ID NO:8); IL-1β: 5'-GGCTCTCCACCTCCTCTCA (SEQ ID NO:9) and 5'-AGCTCATGCAGAACACCTT (SEQ ID NO:10); tumor necrosis factor (TNF)-α: 5'-GCCGGAATACCTGGACTATGC (SEQ ID NO:11) and 5'-CAGGGCGATGATCCCAAAGTAG (SEQ ID NO:12); keratinocyte-derived chemokine (KC): 5'-TGCCAGTGCCTGCAGAC (SEQ ID NO:13) and 5'-AGTGGCTATGACTTCGGTTTGG (SEQ ID NO:14); monocyte chemotactic protein (MCP1): 5'-CCCCGACTATCTGTTTCCACAAC (SEQ ID NO:15) and 5'-CCTGGAAGGGCTTCTGATCTG (SEQ ID NO:16); and ovine ribosomal protein L32 5'-GCAGAAGATTCAAGGGCCAGATC (SEQ ID NO:17) and 5'-GGTTTTCTTGTTGCTCCCGTAAC (SEQ ID NO:18).

Lung tissue of the right middle lobe was homogenized in 0.9% NaCl and supernatant after centrifugation at 1,000×g for 15 minutes and frozen for ELISA of proinflammatory cytokine proteins (Kramer B W, et al. Surfactant protein A recruits neutrophils into the lungs of ventilated preterm lambs. *Am J Respir Crit Care Med* 2001; 163:158-165; Ikegami M, et al. Intratracheal recombinant surfactant protein D prevents endotoxin shock in the newborn preterm lamb. *Am J Respir Crit Care Med* 2006; 173:1342-1347). BALF was recovered from the left lung (Ikegami M, et al. Whitsett J A. Intratracheal recombinant surfactant protein D prevents endotoxin shock in the newborn preterm lamb. *Am J Respir Crit Care Med* 2006; 173:1342-1347) for further analyses. Total proteins were analyzed (Lowry O H, et al. Protein measurement with the Folin phenol reagent. *J Biol Chem* 1951; 193:265-275) in the supernatant of BALF after 10 minutes of centrifugation at 284×g. The right upper lobe was inflation-fixed at 30 cm $H_2O$ for morphology (Ikegami M, et al. Surfactant protein-D regulates the postnatal maturation of pulmonary surfactant lipid pool sizes. *J Appl Physiol* 2009; 106:1545-1552). The amount of rhSP-D in aliquots of BALF was analyzed by ELISA (Ikegami M, et al. Whitsett J A. Intratracheal recombinant surfactant protein D prevents endotoxin shock in the newborn preterm lamb. *Am J Respir Crit Care Med* 2006; 173:1342-1347).

Results are given as means±SEM. Comparisons between +rhSP-D and control groups were made with two-tailed unpaired t tests. For multiple groups, one-way analysis of variance (ANOVA) followed by Bonferroni-Dunn test, or two-way repeated measures ANOVA were used. Significance was accepted at a P value<0.05.

EXAMPLE 2

Lung Function Following rhSP-D Treatment

Six control and six rhSP-D-treated lambs were studied. Sex (three male and three female per group), cord blood pH (7.36±0.04 [control], 7.36±0.05 [+SP-D]), body weight (3.0±0.3 [control], 3.0±0.1 kg [+SP-D]), and lung weight (116±15 [control], 115±5 g [+SP-D]) were similar between +rhSP-D and control groups. Blood pressure, heart rate, hematocrit, glucose, sodium, potassium, and calcium in the blood samples were recorded every 30 minutes and were normal throughout the study period (data not shown). Rectal temperature was maintained at the normal body temperature for sheep (38.5° C.) by means of heating pads, radiant heat, and plastic bodycovering wrap. Ventilation was regulated well for both groups. Lambs were resuscitated with PIP 40 cm $H_2O$ for 20 minutes after birth (FIG. 1A), which resulted in mean $Pco_2$ of 40 mm Hg (FIG. 1B) and $V_T$ of 11 ml/kg (FIG. 1C) for both groups. After surfactant treatment was given at 20 minutes of age, ventilation was changed to regulate $V_T$ at 8 to 9 ml/kg (FIG. 1C) and required a mean PIP of 27 cm $H_2O$ (FIG. 1A) for both groups. These results indicate that lung immaturity, as well as ventilatory stress used to support premature lambs, were comparable between the groups.

Figure 2:
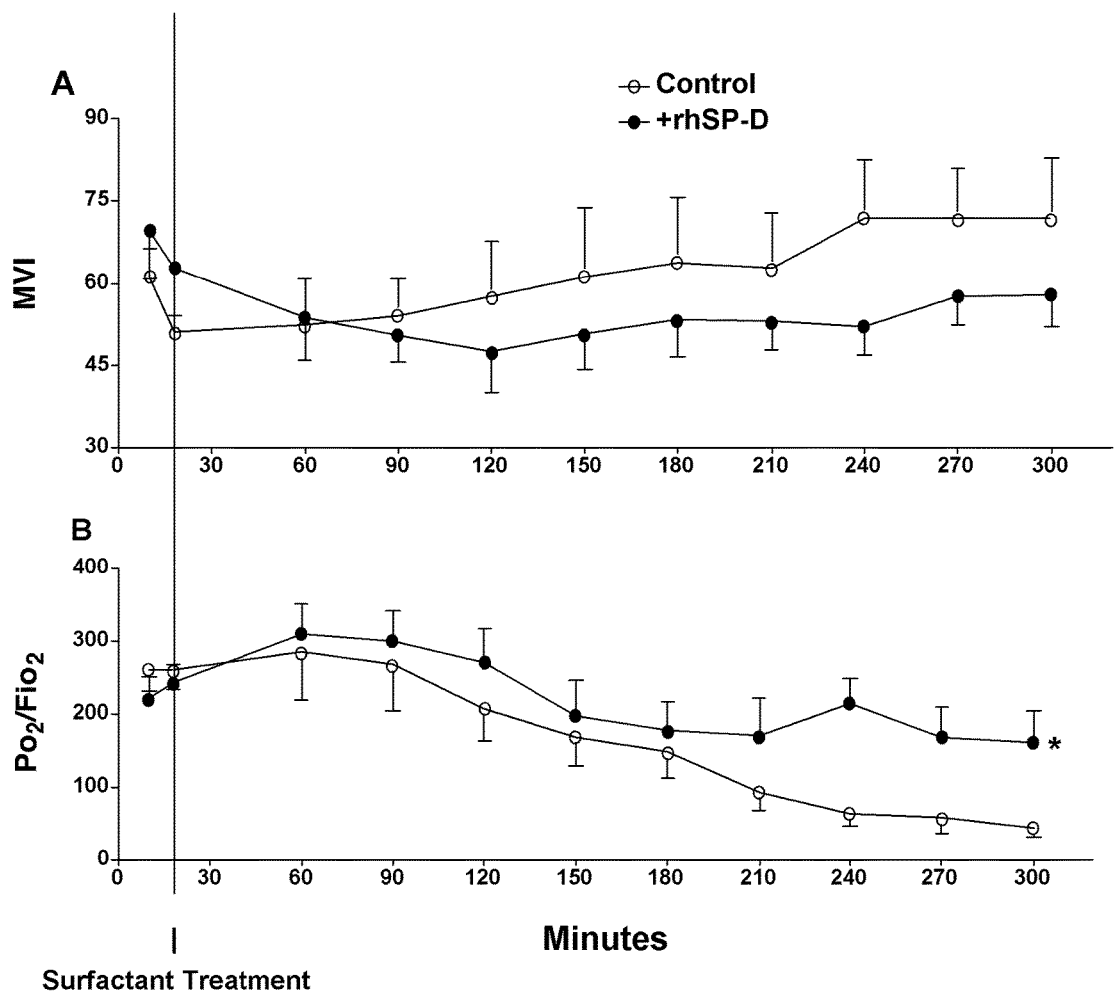
FIG. 2 shows the effects of rhSP-D treatment on lung function. (A) The modified ventilation index (MVI) was calculated as peak inspiratory pressure×$P_{CO2}$×respiratory rate/1,000. Although not significant, MVI tends to be better (lower) for the group treated with rhSP-D (+rhSP-D) at later times. (B) $Po_2/Fio_2$ was higher in the +rhSP-D group compared with the control group (*$P<0.01$ by two-way repeated measures analysis of variance (ANOVA) (overall comparison of control versus+rhSP-D group)). $Po_2/Fio_2$ was significantly decreased after 210 minutes in the control group ($P<0.05$ vs. 18 min by one-way ANOVA).

A modified ventilation index was calculated as PIP×$Pco_2$×respiratory rate/1,000 (Norden M A, et al. Predictors of survival for infants with congenital diaphragmatic hernia. *J Pediatr Surg* 1994; 29:1442-1446). Although it did not reach statistical significance, the mean modified ventilation index was better for the +rhSP-D group after 240 minutes (FIG. 2A). High $Fi_{O2}$ (0.75-1.0) was used for both groups to maintain $P_{O2}$ at the target. Premature lambs at this GA have patent ductus arteriosis, and $P_{O2}/F_{Io2}$ may not be directly associated with lung function. Nevertheless, $P_{O2}/F_{Io2}$ was higher in the +rhSP-D group than the control group (P<0.01 by two-way repeated measures ANOVA) (FIG. 2B). P02/Flo2 was significantly decreased after 210 minutes (P<0.05 by one-way ANOVA) in the control group.

Figure 3:
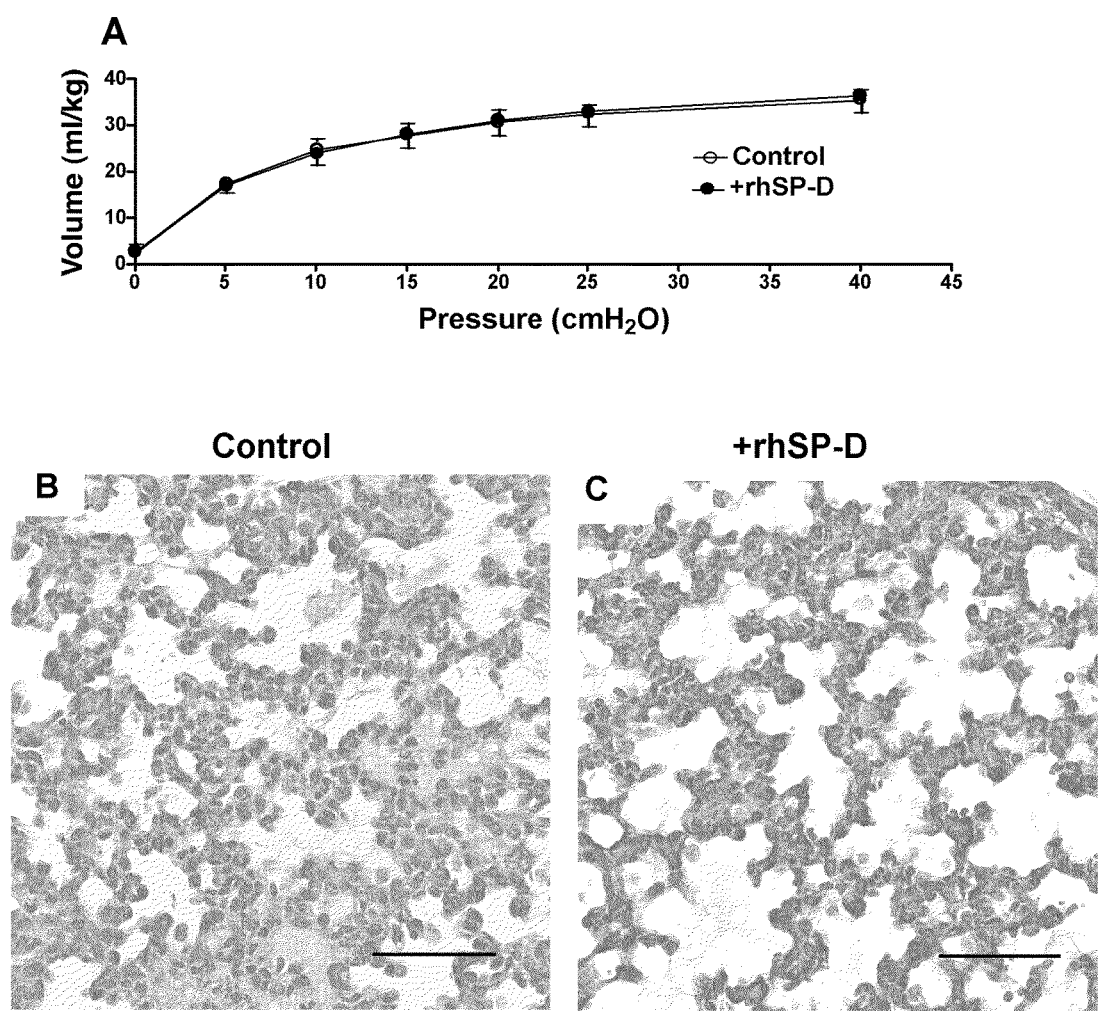
FIG. 3 shows that treatment with rhSP-D does not alter pressure-volume curves or lung histology in premature lambs. (A) The deflation limbs of pressure-volume curves were not different between the rhSP-D treated lambs and controls. (B, C) Lung histology assessed after staining with hematoxylin and eosin was similar for both groups. Histology was typical of immature lung, including thickened alveolar septal walls and patchy atelectasis. More alveolar fluid was observed in control lambs than in lambs treated with rhSP-D (+rhSP-D). Scale bar: 100 μm.

The deflation limb of pressure-volume curves was not different between the groups (FIG. 3A). Likewise, lung morphology was similar for both groups, with typical findings consistent with immaturity, including thickened alveolar septal walls and patchy atelectasis. More fluid was noted in alveoli of the control lambs compared with the +rhSP-D lambs (FIGS. 3B and 3C).

EXAMPLE 3

Pulmonary Inflammation Following rhSP-D Treatment

Previous studies indicated a lack of inflammation as detected in BALF and lung tissue from 130-day GA lambs killed at delivery without ventilation (Naik A S, et al. Effects of ventilation with different positive end-expiratory pressures on cytokine expression in the preteim lamb lung. *Am J Respir Crit Care Med* 2001; 164:494-498; Ikegami M, Jobe A. Postnatal lung inflammation increased by ventilation of pre term lambs exposed antenatally to *E. coli* endotoxin. *Pediatr Res* 2002; 52:356-362).

Figure 4:
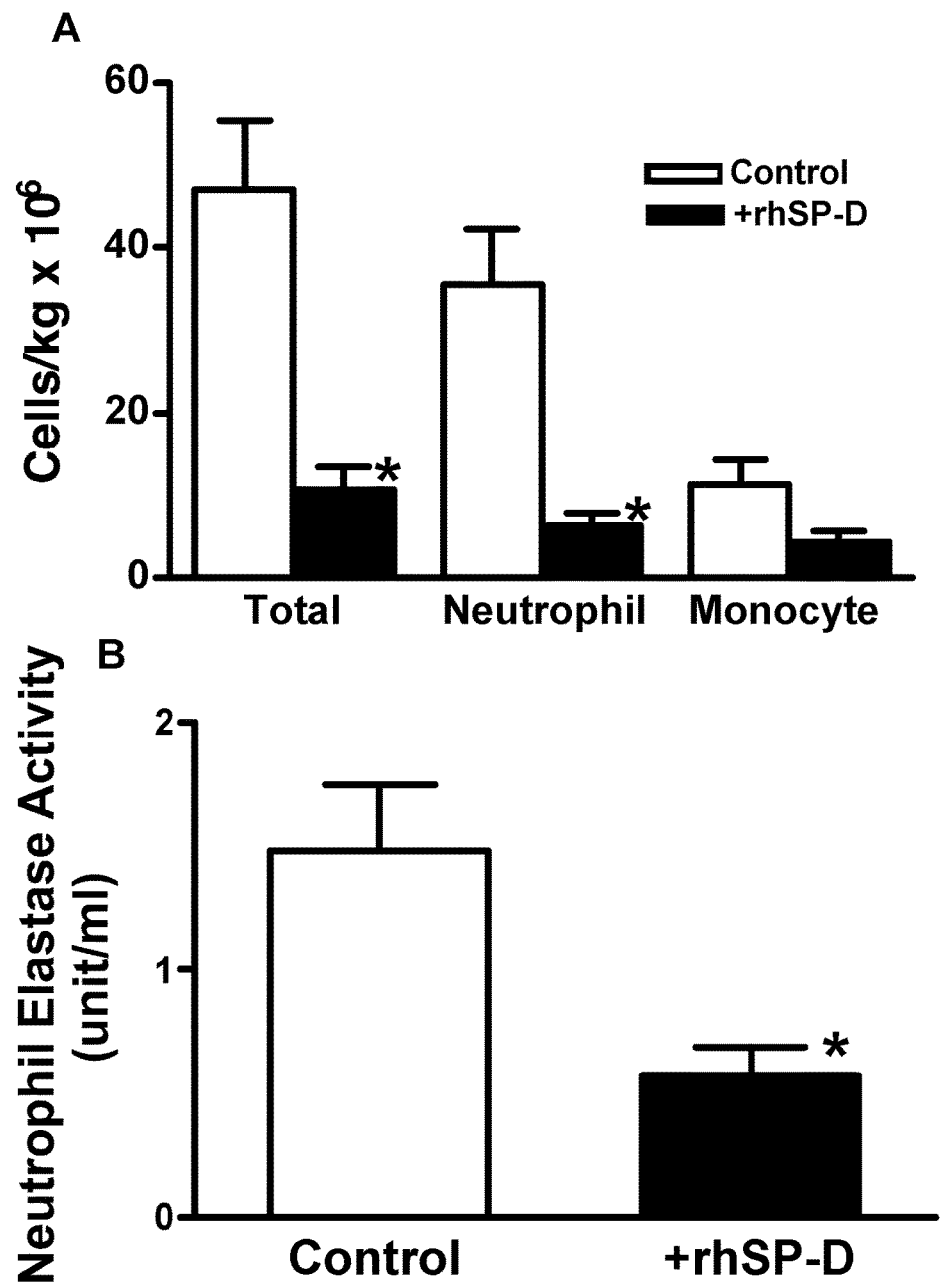
FIG. 4 shows that treatment with rhSP-D decreases the number of inflammatory cells in BALF and decreases neutrophil elastase (NE) activity. (A) Increased total inflammatory cells and neutrophils in BALF induced by ventilation were suppressed by rhSP-D. (B) NE activity was assessed by a spectrophotometric assay using a chromogenic substrate specific for NE. Treatment with rhSP-D-containing SURVANTA® decreased NE activity (*$P<0.05$ versus the control group).
Figure 5:
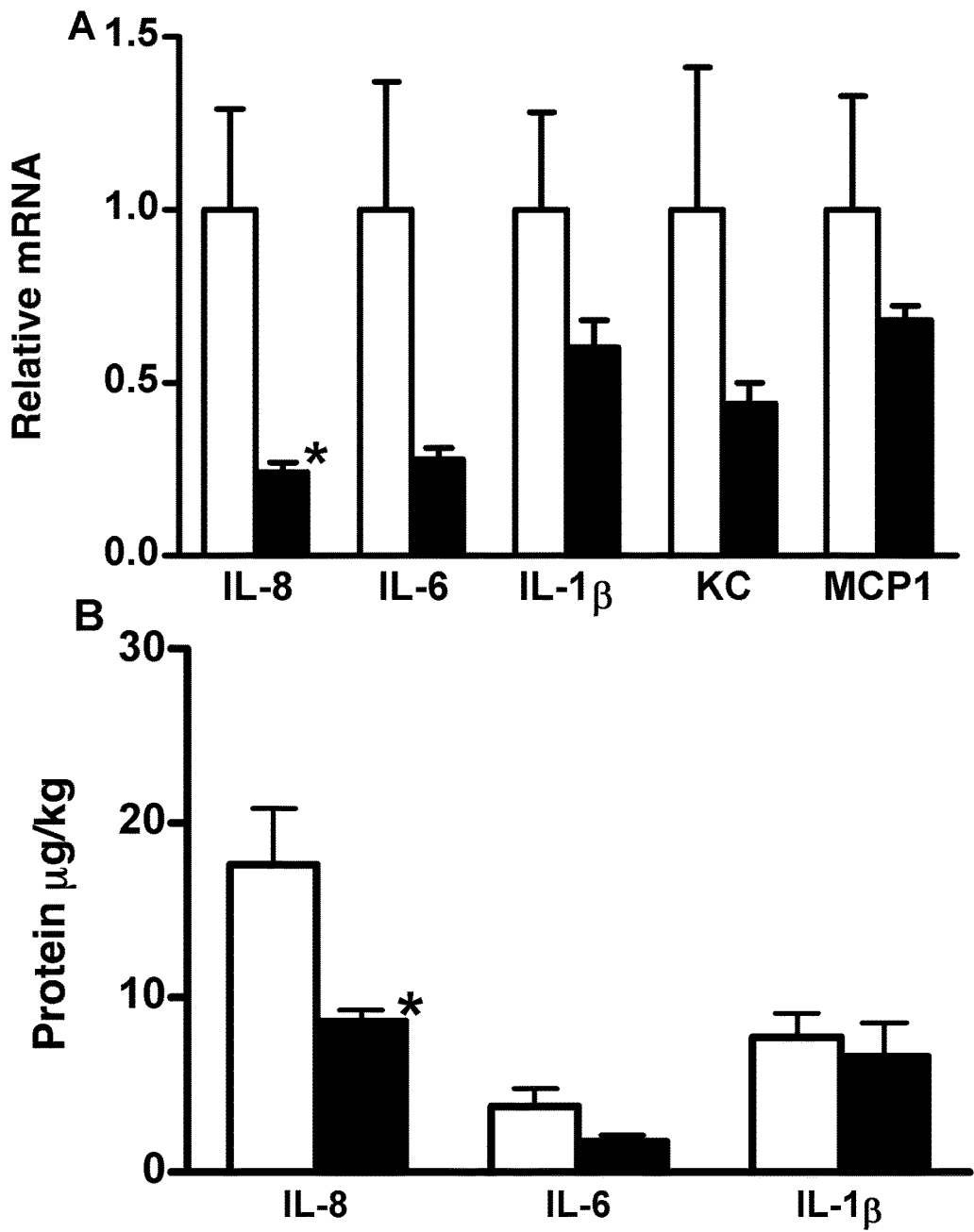
FIG. 5 shows that treatment with rhSP-D decreases the number of proinflammatory markers in lung homogenates. (A) Increased expression of interleukin-8 (IL-8) mRNA was significantly suppressed by rhSP-D treatment. Although not significant (due to the large variation in the control group), mean values of interleukin-6 (IL-6), interleukin-1β (IL-1β), keratinocyte-derived chemokine (KC), and monocyte chemotactic protein 1 (MCP1) were generally lower in the +rhSP-D group. (B) IL-8 protein in lung homogenates was significantly decreased by rhSP-D treatment (*$P<0.05$ versus the control group), while IL-1β was not influenced by rhSP-D treatment.

Despite the use of a lung-protective ventilatory strategy, five hours of ventilation was associated with lung inflammation in the control lambs. In contrast, lung inflammation was decreased in all the lambs treated with rhSP-D. Inflammatory cells in the pellets collected by centrifugation were counted using trypan blue and differential cell counts were performed on the stained cytospin preparation (Kramer B W, et al. Surfactant protein A recruits neutrophils into the lungs of ventilated preterm lambs. *Am J Respir Crit Care Med* 2001; 163:158-165; Naik A S, et al. Effects of ventilation with different positive end-expiratory pressures on cytokine expression in the preterm lamb lung. *Am J Respir Crit Care Med* 2001; 164:494-498). Total inflammatory cell numbers and neutrophils were significantly decreased by rhSP-D (FIG. 4A). Increased NE activity has been associated with the development of BPD (Watterberg K L, et al. Secretory leukocyte protease inhibitor and lung inflammation in developing bronchopulmonary dysplasia. *J Pediatr* 1994; 125: 264-269; Yasumatsu R, et al. SERPINB1 upregulation is associated with in vivo complex formation with neutrophil elastase and cathepsin G in a baboon model of bronchopulmonary dysplasia. *Am J Physiol Lung Cell Mol Physiol* 2006; 291:L619-L627). The addition of rhSP-D to SURVANTA® decreased NE activity in the lung (FIG. 4B). Expression of IL-8, IL-6, IL-1β, TNF-α, KC, and MCP1 mRNA were analyzed by reverse transcriptase-polymerase chain reaction (FIG. 5A), and IL-8, IL-6, and IL-1β proteins in the supernatants of lung homogenates were measured by ELISA (FIG. 5B). Ovine ribosomal protein L32 was used as a reference RNA. Proinflammatory cytokine IL-8 (mRNA and protein), which plays a major role in neutrophil recruitment, was significantly decreased in the lung of rhSP-D-treated lambs. Although not statistically significant, mean IL-6 mRNA expression (P=0.06), and IL-6 protein (P=0.1) in the lung were lower in the +rhSP-D group. IL-1β protein and mRNA were not significantly influenced by rhSP-D treatment. Expression of TNF-α mRNA was similarly present at low levels in both groups (data not shown). KC, a functional homolog of IL-8, is critical for neutrophil recruitment and known to increase in ventilation-induced lung injury in adults (Belperio J A, et al. Critical role for CXCR2 and CXCR2 ligands during the pathogenesis of ventilator-induced lung injury. *J Clin Invest* 2002; 110:1703-1716). MCP1 possesses potent chemotactic activity for monocytes. Because of the large variation in lung inflammation in the control lambs, KC and MCP1 mRNA in the lung were not significantly different between the two groups, although mean levels were decreased by rhSP-D treatment.

The CD45 antibody recognizes the leukocyte common antigen and is present on cells of hematopoietic origin, except for erythroid cells and platelets. CD45-positive cells were isolated from BALF using magnetic cell separation (Miltenyi Biotech Inc., Auburn, Calif.) and CD14, CD11b, and CD44 were analyzed by flow cytometry (data not shown). CD14-positive cells were not detected in either group, suggesting that lung inflammation was not associated with infection. Both CD11b and CD44 influence vascular-to-tissue migration of neutrophils and monocytes to the sites of inflammation (Weirich E, et al. Neutrophil CD11b expression as a diagnostic marker for early-onset neonatal infection. *J Pediatr* 1998; 132:445-451). Treatment with rhSP-D did not influence expression of CD11b or CD44, suggesting that suppression of neutrophil recruitment by rhSP-D in the lung was independent of changes in CD11 b and CD44.

After instillation of 7 mg of rhSP-D, 6.7±0.2 mg rhSP-D was recovered in BALF 4.7 hours after treatment. The slow clearance of exogenous rhSP-D from the lung is consistent with previous findings (Ikegami M, Jobe A H. Surfactant metabolism. *Semin Perinatol* 1993; 17:233-240), supporting the low rate of surfactant clearance in the preterm lung. Human SP-D was not detected in BALF from control lambs.

EXAMPLE 4

Increased Resistance Against Surfactant Inhibition Following rhSP-D Treatment

Surface tension was measured by captive bubble surfactometer (Schoel M, et al. The captive bubble method for the evaluation of pulmonary surfactant: surface tension, area, and volume calculations. *Biochim Biophys Acta* 1994; 1200: 281-290) on 3 µL of samples containing 15 µg/µL SURVANTA® and 2% rhSP-D or buffer in the presence or absence of surfactant inhibitor (21 µg/µL plasma protein) (Ikegami M, et al. Characteristics of surfactant from SP-A deficient mice. *Am J Physiol Lung Cell Mol Physiol* 1998; 275:L247-L25). This amount of plasma protein relative to SURVANTA® was 30% lower than the concentration that is known to inhibit the activity of SURVANTA® in the ventilated premature newborn lamb lung in vivo (Wada K, et al. Tidal volume effects on surfactant treatment responses with the initiation of ventilation in preterm lambs. *J Appl Physiol* 1997; 83:1054-1061). The influence of rhSP-D on the ultrastructure of SURVANTA® was studied as previously described (Schmiedl A, et al. Influence of plasma and inflammatory proteins on the ultrastructure of exogenous surfactant. *J Electron Microsc (Tokyo)* 2004; 53:407-416).

Figure 6:
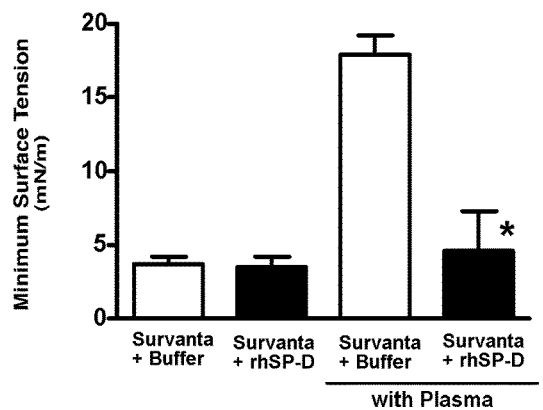
FIG. 6 shows that the addition of rhSP-D to surfactant increased resistance against surfactant inhibition. (A) Surface tension was measured by a captive bubble surfactometer. SURVANTA®+buffer had high surface activity, and minimum surface tension was low and was not influenced by addition of rhSP-D. Plasma protein inhibited the surface tension-lowering properties of SURVANTA®, and minimum surface tension was increased. The addition of rhSP-D rendered the SURVANTA® more resistant to plasma protein inhibition, with low minimum surface tension in the presence of plasma protein (n=3, *$P<0.05$ versus SURVANTA®+buffer with plasma). (B, C) Representative electron micrographs of SURVANTA® mixed with buffer or rhSP-D. Addition of rhSP-D changed the ultrastructure of SURVANTA® from simple lipid layers to the mixture of multiple lipid layers and lipid aggregates (n=3 per group). Scale bar: 500 nm.
Figure 6:
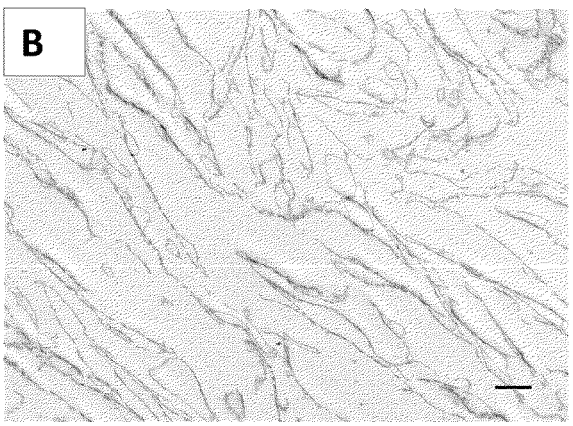
Figure 6:
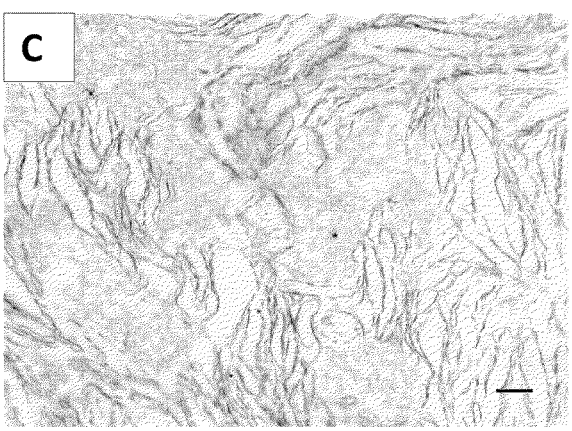

Minimum surface tension of SURVANTA® with (+rhSP-D) or without rhSP-D (+buffer) in the presence or absence of a surfactant inhibitor (plasma protein) was measured with a captive bubble surfactometer (FIG. 6A). The minimum surface tension was low with or without rhSP-D—consistent with the high surface activity of SURVANTA® and similarity of lung function and pressure-volume curves seen in both +rhSP-D-treated and control lambs. Immediately after mixing with plasma, surfactant mixtures were applied to the bubble. Plasma proteins inhibited the surface tension-lowering properties of SURVANTA®, with the minimum surface tension being increased to greater than 15 mN/m. The addition of 2% rhSP-D to SURVANTA® rendered the SURVANTA® more resistant to plasma protein inhibition, the minimum surface tension remaining low in the presence of plasma proteins. Because SP-D influences surfactant ultrastructure in the alveolus by causing lysis of surfactant lipid layers (Ikegami M, et al. Surfactant protein-D regulates the postnatal maturation of pulmonary surfactant lipid pool sizes. *J Appl Physiol* 2009; 106:1545-1552), ultrastructure of the surfactant mixtures used for treatment was assessed. The simple lipid layers formed by SURVANTA® (FIG. 6B) were changed by the addition of rhSP-D, causing the formation of lipid aggregates and multilayers (FIG. 6C). These changes in the ultrastructure of SURVANTA® caused by rhSP-D may be related to its resistance to inhibition of surface activity by plasma protein. Although proteins in BALF in both the control group (60±7 mg/kg) and +rhSP-D group (57±11 mg/kg) were threefold higher than that in non-ventilated premature lambs seen in previous studies (Naik A S, et al. Effects of ventilation with different positive end-expiratory pressures on cytokine expression in the preterm lamb lung. *Am J Respir Crit Care Med* 2001; 164:494-498; Ikegami M, Jobe A. Postnatal lung inflammation increased by ventilation of pretemi lambs exposed antenatally to *E. coli* endotoxin. *Pediatr Res* 2002; 52:356-362), they were not high enough to inhibit the function of the large amount of SURVANTA® given to the lambs. Inhibition of surfactant function by plasma protein occurs when alveolar proteins are increased above 200 mg/kg (Wada K, et al. Tidal volume effects on surfactant treatment responses with the initiation of ventilation in preterm lambs. *J Appl Physiol* 1997; 83:1054-1061).

EXAMPLE 5 rhSP-D and Animal Surfactant Treatment in a Premature Infant rhSP-D and natural animal surfactants, including SURVANTA®, INFASURF®, and CUROSURF®, are administered to premature infants. The combinations of rhSP-D and each of the natural animal surfactants are tested clinically against the natural surfactants alone (i.e., a test for superior effects). The premature infants are assessed clinically for the prevention and/or treatment of neonatal respiratory distress syndrome (RDS), and for the prevention of bronchopulmonary dysplasia (as these conditions are defined by one of skill in the art at the time of the study). Study endpoints include the percentage of infants recovering from RDS and the incidence of BPD in the study population.

EXAMPLE 6 rhSP-D and Synthetic Surfactant Treatment in a Premature Infant rhSP-D and a synthetic surfactant, with or without any component of surfactant protein, are administered to premature infants. The combination of rhSP-D and the synthetic surfactant is tested clinically against the synthetic surfactant alone (i.e., a test for superiority), and/or a natural surfactant alone (i.e., a test for superiority), and/or the combination of rhSP-D and a natural surfactant (i.e., a test for equivalence or superiority). The premature infants are assessed clinically for the prevention and/or treatment of neonatal respiratory distress syndrome (RDS), and for the prevention of bronchopulmonary dysplasia (as these conditions are defined by one of skill in the art at the time of the study). Study endpoints include the percentage of infants recovering from RDS and the incidence of BPD in the study population.

What is claimed is:

1. A method of treating a subject having a pulmonary disorder selected from the group consisting of a pulmonary injury resulting from mechanical ventilation, neonatal respiratory distress syndrome, a pulmonary injury resulting from administration of oxygen, and a bronchopulmonary dysplasia, comprising administering an effective amount of a surfactant in combination with an effective amount of surfactant protein D (SP-D) to the subject, wherein the effective amount of the surfactant is less than the effective amount of the surfactant in the absence of the SP-D, and is sufficient to treat the pulmonary disorder.

2. The method of claim 1, wherein the pulmonary disorder is a pulmonary injury resulting from administration of oxygen.

3. The method of claim 1, wherein the pulmonary disorder is a pulmonary injury resulting from mechanical ventilation.

4. The method of claim 1, wherein the amount of the SP-D) is sufficient to reduce the activity of an endogenous surfactant inhibitor in a lung of the subject.

5. The method of claim 4, wherein the endogenous surfactant inhibitor comprises a plasma protein.

6. The method of claim 1, wherein the amount of the SP-D is sufficient to reduce the activity of an endogenous surfactant inhibitor on the surface tension lowering properties of the surfactant in a lung of the subject.

7. The method of claim 1, wherein the amount of the SP-D is sufficient to reduce the surface tension lowering properties of the surfactant in a lung of the subject by about 4-fold compared to the surface tension lowering properties of the surfactant in the presence of an endogenous surfactant inhibitor in a lung of the subject and in the absence of the SP-D.

8. The method of claim 1, wherein the SP-D is recombinant human SP-D or a functional fragment thereof.

9. The method of claim 1, wherein the surfactant and SP-D) are administered in a single pharmaceutical composition.

10. The method of claim 9, wherein the pharmaceutical composition comprises about 2% SP-D.

11. The method of claim 9, wherein the pharmaceutical composition comprises a phospholipid selected from the group consisting of dipalmitoylphosphatidylcholine, phosphatidylglycerol, and phosphatidylinositol.

12. The method of claim 9, wherein the surfactant and SP-D are administered in an aerosolized form.

13. The method of claim 9, wherein the surfactant and SP-D are administered in a dry powder form.

14. The method of claim 1, wherein the dose of the SP-D is about 0.1 mg/kg to about 10 mg/kg body weight of the subject.

15. The method of claim 1, wherein the dose of the SP-D is about 2 mg/kg body weight of the subject.

16. The method of claim 1, wherein the surfactant is an animal product.

17. The method of claim 1, wherein the surfactant is bovine surfactant.

18. The method of claim 1, wherein the surfactant is synthetic surfactant.

19. The method of claim 1, wherein the subject is a neonate.

20. The method of claim 1, wherein the subject is a preterm neonate.

* * * * *

UNITED STATES PATENT AND TRADEMARK OFFICE
CERTIFICATE OF CORRECTION

PATENT NO. : 10,159,716 B2
APPLICATION NO. : 15/341383
DATED : December 25, 2018
INVENTOR(S) : Jeffrey A. Whitsett It is certified that error appears in the above-identified patent and that said Letters Patent is hereby corrected as shown below:

On the Title Page

Page 2, Column 1, item [56], Line 40, delete "274(1 Pt 1)L97-105." and insert --274(1 Pt 1):L97-105.--.

Page 3, Column 1, item [56], Line 21, delete "spetic ards:" and insert --septic ards:--.

Page 3, Column 1, item [56], Line 27, delete "homeostatis" and insert --homeostasis--.

Page 3, Column 2, item [56], Line 40, delete "clongin," and insert --cloning,--.

Page 3, Column 2, item [56], Line 52, delete "(275(1):56-62." and insert --275(1):56-62.--.

Page 4, Column 1, item [56], Line 65, delete "proein" and insert --protein--.

Page 4, Column 2, item [56], Line 51, delete "2006;291:L619-L627)." and insert --2006;291:L619-L627.--.

In the Specification

Column 9, Line 21, delete "pretemi" and insert --preterm--.

Column 10, Line 62, delete "protein" and insert --protein 1--.

Column 12, Line 23, delete "preteim" and insert --preterm--.

Column 14, Line 25, delete "pretemi" and insert --preterm--.

Signed and Sealed this
Eighteenth Day of February, 2020

Andrei Iancu
*Director of the United States Patent and Trademark Office*

CERTIFICATE OF CORRECTION (continued)
U.S. Pat. No. 10,159,716 B2

In the Claims

Column 25, Line 29, Claim 4, delete "SP-D)" and insert --SP-D--.

Column 26, Line 15, Claim 9, delete "SP-D)" and insert --SP-D--.